United States Patent
Sohn et al.

(10) Patent No.: US 8,475,362 B2
(45) Date of Patent: Jul. 2, 2013

(54) SURGICAL APPARATUS FOR TRANSANAL ENDOSCOPIC MICROSURGERY

(75) Inventors: Dae-Kyung Sohn, Gyeonggi-do (KR);
Dae-Hyun Kim, Gyeonggi-do (KR);
Kwang-Gi Kim, Gyeonggi-do (KR);
Kyoung-Won Nam, Gyeonggi-do (KR);
Hyung-Tae Kim, Gyeonggi-do (KR)

(73) Assignee: National Cancer Center, Gyeonggi-Do (KR)

( * ) Notice: Subject to any disclaimer, the term of this patent is extended or adjusted under 35 U.S.C. 154(b) by 598 days.

(21) Appl. No.: 12/725,003

(22) Filed: Mar. 16, 2010

(65) Prior Publication Data
US 2010/0331620 A1     Dec. 30, 2010

(30) Foreign Application Priority Data

Jun. 29, 2009    (KR) .................. 10-2009-0058063
Jul. 31, 2009    (KR) .................. 10-2009-0070343

(51) Int. Cl.
*A61B 1/04*      (2006.01)

(52) U.S. Cl.
USPC ............ 600/114; 600/105; 600/137; 600/204

(58) Field of Classification Search
USPC .......................... 600/105, 114, 137, 204–206
See application file for complete search history.

(56) References Cited

U.S. PATENT DOCUMENTS

| | | | |
|---|---|---|---|
| 4,112,932 A | 9/1978 | Chiulli | |
| 4,538,594 A | 9/1985 | Boebel et al. | |
| 5,486,155 A * | 1/1996 | Muller et al. | 600/137 |
| 5,843,040 A * | 12/1998 | Exline | 604/164.11 |
| 5,928,137 A * | 7/1999 | Green | 600/160 |
| 6,142,931 A * | 11/2000 | Kaji | 600/114 |
| 6,458,077 B1 | 10/2002 | Boebel et al. | |
| 7,452,329 B2 * | 11/2008 | Bastia et al. | 600/184 |
| 7,611,458 B2 * | 11/2009 | Sias | 600/136 |
| 7,695,432 B2 * | 4/2010 | Scheyer | 600/184 |

(Continued)

FOREIGN PATENT DOCUMENTS

| | | |
|---|---|---|
| DE | 8233240 | 3/1983 |
| DE | 3319049 | 5/1984 |
| DE | 2226026 | 9/2010 |

OTHER PUBLICATIONS

Extended European Search Report—(EP10155841) Date of completion of the search Nov. 2, 2010.

*Primary Examiner* — Matthew J Kasztejna
(74) *Attorney, Agent, or Firm* — Foley & Lardner LLP; Michel Morency

(57) ABSTRACT

Provided is a surgical apparatus for transanal endoscopic microsurgery (TEM) in which a thin and long endoscope and surgical instruments are inserted through a natural orifice of a human body and the endoscope and surgical instruments are conveyed to the operation area in the body to perform the operation area in the body. According to the surgical apparatus for TEM, a rotation function is added to a barrel of the surgical apparatus for TEM to enable manual rotation of the barrel to a required extent and adjustment of an operation area, without separation of the surgical apparatus for TEM from a fixing frame during an operation. In addition, since the endoscope is disposed outside the barrel, it is possible to reduce the outer diameter of the barrel and uniformly maintain a visual direction of the endoscope even when the barrel is rotated. Further, since the rotation function is added to both the barrel and the surgical instrument insertion hole, more convenient operation is possible.

19 Claims, 29 Drawing Sheets

U.S. PATENT DOCUMENTS

2006/0155169 A1* 7/2006 Bastia et al. .................. 600/199
2010/0228092 A1* 9/2010 Ortiz et al. .................... 600/204
2010/0228094 A1* 9/2010 Ortiz et al. .................... 600/205
2011/0015491 A1* 1/2011 Ravikumar et al. ........... 600/233

* cited by examiner

B - B

C - C

SURGICAL APPARATUS FOR TRANSANAL ENDOSCOPIC MICROSURGERY

CROSS-REFERENCE TO RELATED APPLICATION

This application claims priority to and the benefit of South Korean Patent Application No. 10-2009-0058063, filed Jun. 29, 2009, and No. 10-2009-0070343, filed Jul. 31, 2009, the disclosure of which is incorporated herein by reference in its entirety.

BACKGROUND

1. Field of the Invention

The present invention relates to a surgical apparatus for transanal endoscopic microsurgery (TEM).

2. Discussion of Related Art

In general, conventional open surgery for patient treatments causes delay of post-surgical recovery for the patients due to a large incision area and thus a heavy loss of blood, and large scars remaining after the surgery have a negative impact on the patients' lives after the surgery. In order to overcome the above disadvantages of the conventional open surgery, in recent times, novel surgical techniques such as minimally invasive surgery (MIS), natural orifice transluminal endoscopic surgery (NOTES), etc., have been developed.

MIS is a surgical technique of incising and operating on a minimal area of a patient's body using a thin and long surgical instrument specifically configured to minimize an incision area for surgery, and NOTES is a surgical technique of inserting a surgical instrument through a natural orifice (for example, the esophagus, the anus, the vagina, etc.) of a human body and conveying the surgical instrument to the operation area in the body to operate on the area without incising the patient's body in order to move the surgical instrument to the operation area in the body. Since MIS and NOTES require only a small incision area for operation and a loss of blood is remarkably less than that of the open surgery, a post-surgical recovery time for the patient is shortened and scarring is minimal. Therefore, in recent times, the number of MIS and NOTES operations has remarkably increased.

As an example of the NOTES, a surgical apparatus for transanal endoscopic microsurgery (TEM) is used. This apparatus is inserted into the anus of a patient so that a thin and long surgical instrument and an endoscopic instrument are conveyed to an affected area of the patient through an inner space thereof to perform a surgical operation.

The conventional surgical apparatus for TEM is configured to allow a surgeon to easily perform an operation by changing a patient's posture according to the position of the affected area. After the initial positioning, the apparatus is connected to a fixing frame to prevent further movement of the apparatus. However, when lateral rotation of the surgical apparatus for TEM is needed during the operation, there are many inconveniences such as changes of the patient's posture or separation of the apparatus from the fixing frame, re-positioning of the fixing frame, and rotation and fixation of the apparatus to the fixing frame.

In addition, when the conventional surgical apparatus for TEM is entirely rotated, since an endoscope connected to the apparatus is also rotated therewith, an endoscope screen is unintentionally rotated to cause inconvenience of re-adjustment of the posture of the endoscope.

Further, since the conventional surgical apparatus for TEM is disposed in a barrel together with the endoscope and various surgical instruments, an outer diameter of the barrel is enlarged to increase probability of injury to the patient's anus, and interference between the endoscope and the surgical instruments occurs, making it difficult to freely move the surgical instruments.

SUMMARY OF THE INVENTION

The present invention is directed to a surgical apparatus for TEM capable of adjusting an operation area by adding a rotation function to a barrel of the surgical apparatus for TEM, without separation of the surgical apparatus from a fixing frame during an operation.

The present invention is also directed to a surgical apparatus for TEM capable of readily enlarging the operation area by rotating the barrel to obtain a visual field of the operation.

The present invention is also directed to a surgical apparatus for TEM capable of uniformly maintaining the visual field of the operation even when the barrel is rotated.

The present invention is also directed to a surgical apparatus for TEM capable of preventing interference between the endoscope and the surgical instruments inserted into the apparatus.

The present invention is also directed to a surgical apparatus for TEM capable of reducing the outer diameter of the barrel to minimize injury to a patient's anus.

Additional aspects of the invention will be set forth in the description which follows, and in part will be apparent from the description, or may be learned by practice of the invention.

In an example embodiment, a surgical apparatus for transanal endoscopic microsurgery (TEM) includes: a main body having an endoscope insertion port through which an endoscope for TEM is inserted and a surgical instrument insertion port through which surgical instruments are inserted, the surgical instrument insertion port being independently rotated from the endoscope insertion port; a rotary part rotatably coupled to a front end of the main body and through which the endoscope and the surgical instruments inserted into the main body pass; and a barrel coupled to a front end of the rotary part to be integrally rotated according to rotation of the rotary part, and inserted into the patient's anus to form a guide path for the endoscope and the surgical instruments.

In addition, the main body may include: a housing having a front end to which the rotary part is rotatably coupled, and through which the endoscope and the surgical instrument pass; a tool insertion part coupled to a rear surface of the housing and in which the endoscope insertion port is formed; a surgical instrument insertion part rotatably installed at the tool insertion part and in which the surgical instrument insertion port is formed; and a locking part disposed between the housing and the tool insertion part and configured to lock the tool insertion part to the housing.

Further, the housing may be configured to differentiate an endoscope through-hole through which the endoscope passes from a surgical instrument through-hole through which the surgical instrument passes.

Furthermore, the housing may include a gas discharge pipe configured to discharge an unnecessary internal gas, which may be generated during the operation, to the exterior, and a gas injection pipe configured to inject a gas therein to obtain an operation space.

In addition, a rotary shaft projection may be formed at a center of a rear surface of the tool insertion part such that the operation instrument insertion part is laterally rotatably coupled to the tool insertion part, and a rotary shaft groove may be formed at a rotation center of the surgical instrument insertion part to receive the rotary shaft projection.

Further, the tool insertion part may have a surgical instrument through-hole opened around the rotary shaft projection to include a rotation angle range of the surgical instrument insertion port.

Furthermore, the tool insertion part may include a rotation guide member configured to support the surgical instrument insertion part to be rotatably guided.

In addition, the tool insertion part may include a tool insertion cover configured to prevent separation of the surgical instrument insertion part supported by the rotation guide member.

Further, the surgical instrument insertion part may have an anti-interference groove formed at a periphery of the surgical instrument insertion part opposite to the endoscope and corresponding to the rotation angle range of the surgical instrument insertion part to prevent interference with the endoscope upon rotation thereof.

Furthermore, the locking part may be rotated and locked to a rear end of the housing, and the tool insertion part may be inserted and coupled to the locking part.

In addition, a rotation angle adjustment unit may be installed between the main body and the rotary part to uniformly adjust a rotation angle of the rotary part in a stepped manner when the rotary part is rotated with respect to the main body.

Here, an embodiment of the rotation angle adjustment unit may include at least one click ball provided on a circumference of a front surface of the main body, and a plurality of click grooves formed at a circumference of a rear surface of the rotary part at predetermined intervals. The click ball may be inserted into the click grooves in a stepped manner to rotate the rotary part to a certain angle with respect to the main body when the rotary part is rotated.

In addition, another embodiment of the rotation angle adjustment unit may include at least one first ring installed at an outer periphery of a front surface of the main body, and a plurality of second rings installed along an inner periphery of a rear surface of the rotary part at predetermined intervals. The first ring may be in contact with the second rings in a rotation direction thereof in a stepped manner to rotate the rotary part to a certain angle with respect to the main body when the rotary part is rotated. Here, at least one of the first and second rings may be a rotary ring.

Further, an anti-separation unit may be provided between the main body and the rotary part to prevent separation of the rotary part from the main body.

Here, the anti-separation unit may include an anti-separation groove formed along an outer periphery of a front end of the main body, and an anti-separation screw inserted through a screw hole formed at a position of the rotary part corresponding to the anti-separation groove to be hooked by the anti-separation groove.

In addition, the barrel may include an inclined opening surface formed at its tip and having an opening inclined in a longitudinal direction of the barrel, and an enlarged opening surface configured to enlarge a lower area of the opening by extending a lower part of the inclined opening surface rearward.

Further, in the surgical apparatus for TEM, the endoscope inserted into the main body and passing through the rotary part may be disposed outside the barrel, and the surgical instrument may be disposed in the barrel.

Furthermore, the barrel may include an endoscope opening surface having an opening corresponding to the tip of the endoscope disposed outside the barrel.

In addition, the surgical apparatus for TEM may further include a barrel fixing part coupled to the front end of the rotary part and configured to fix the barrel to the rotary part.

Further, the barrel fixing part may be threadedly engaged with the rotary part to fix the barrel to the rotary part. For this purpose, a male thread may be formed at an outer periphery of the front end of the rotary part, and a female thread may be formed at an inner periphery of the barrel fixing part to be threadedly engaged with the male thread.

Furthermore, the barrel fixing part may have a barrel insertion hole through which the barrel is inserted.

In addition, at least two fixing projections may be formed at a rear end of the barrel, and the same number of fixing holes as the fixing projections are formed at a front end of the rotary part to receive the fixing projections.

Further, the surgical apparatus for TEM may further include a main body supporter coupled to the main body.

In an example embodiment, a surgical apparatus for transanal endoscopic microsurgery (TEM) includes: a main body into which an endoscope and surgical instruments for TEM are inserted; a rotary part rotatably coupled to a front end of the main body and through which the endoscope and the surgical instruments inserted into the main body pass; and a barrel coupled to a front end of the rotary part to be integrally rotated according to rotation of the rotary part, and inserted into the patient's anus to form a guide path for the endoscope and the surgical instruments.

Specific descriptions of other example embodiments will be apparent from the detailed description and the attached drawings.

BRIEF DESCRIPTION OF THE DRAWINGS

The above and other objects, features and advantages of the present invention will become more apparent to those of ordinary skill in the art by describing in detail example embodiments thereof with reference to the attached drawings, in which.

DETAILED DESCRIPTION OF EXAMPLE EMBODIMENTS

Figure 1:
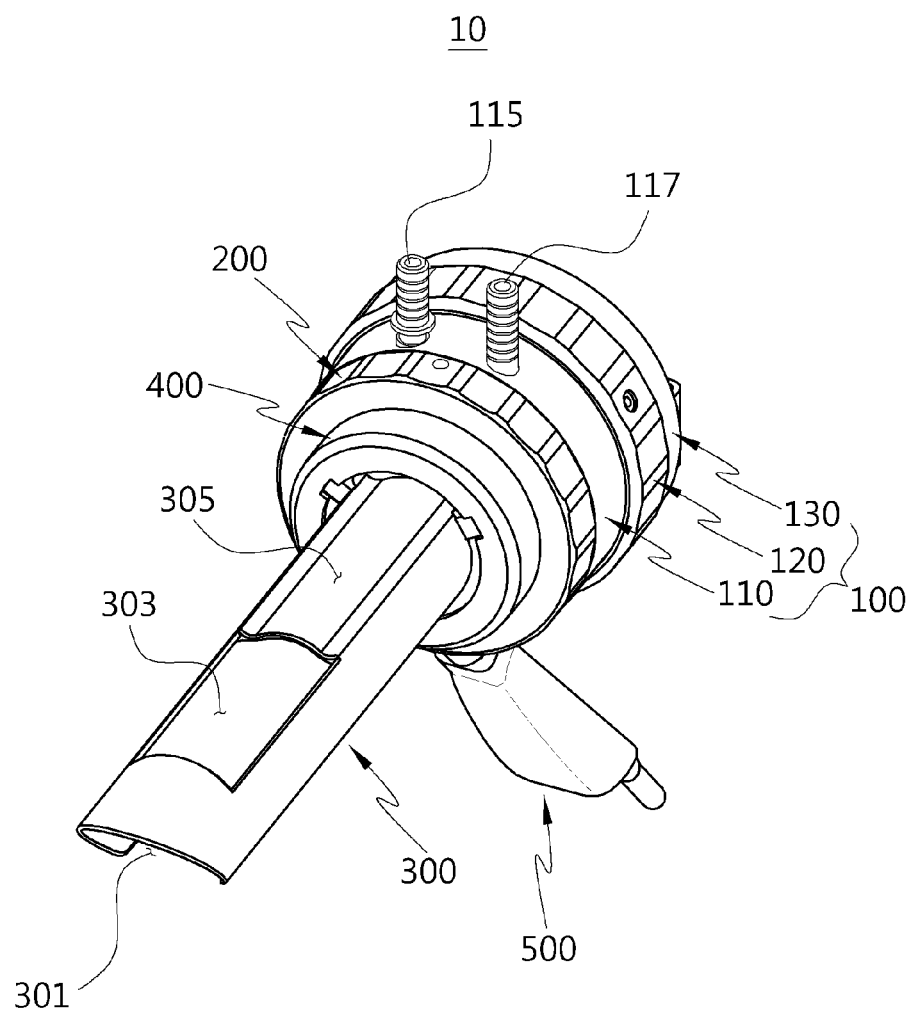
FIGS. 1 and 2 are front and rear perspective views of a surgical apparatus for TEM in accordance with an example embodiment of the present invention.
Figure 2:
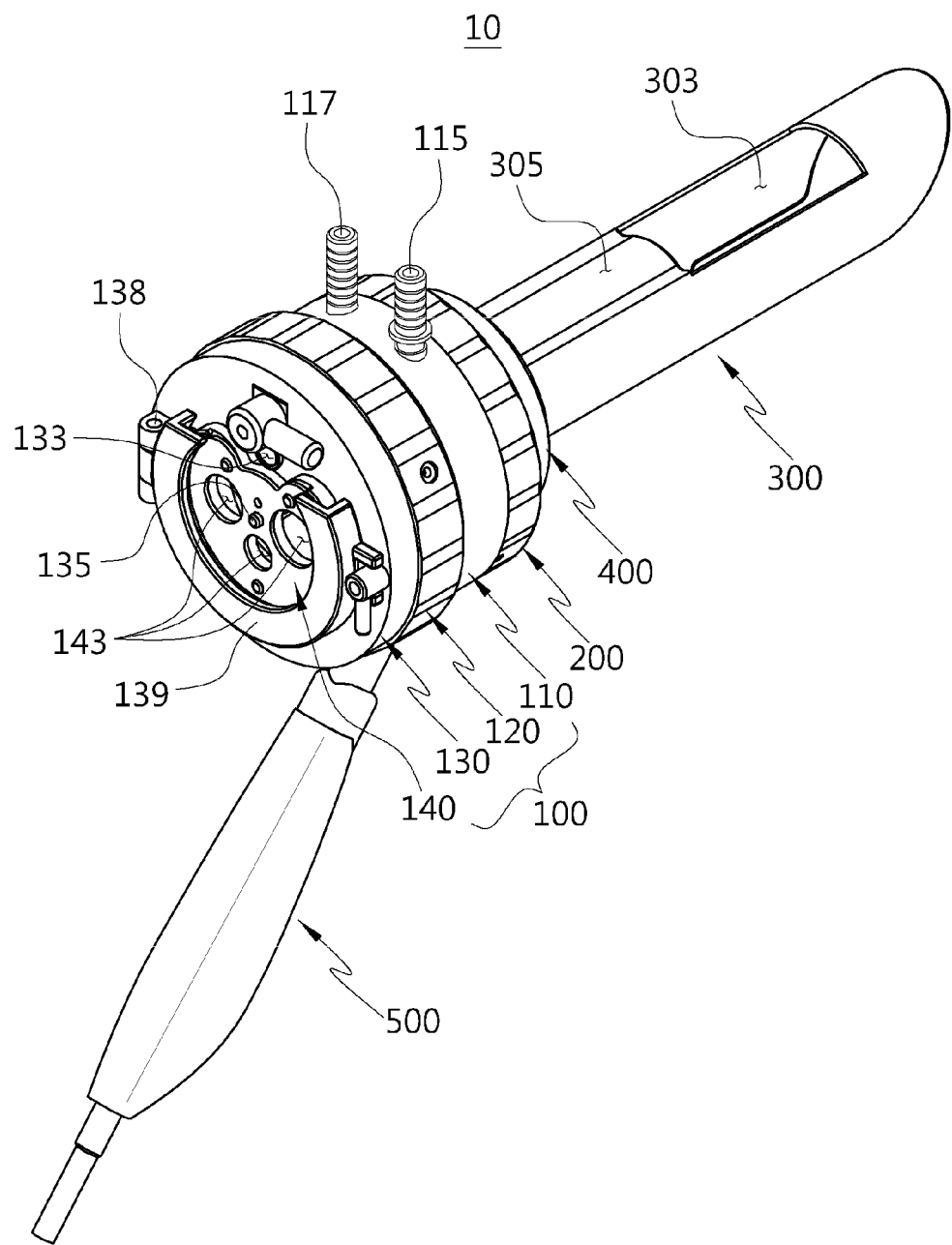
Figure 3:
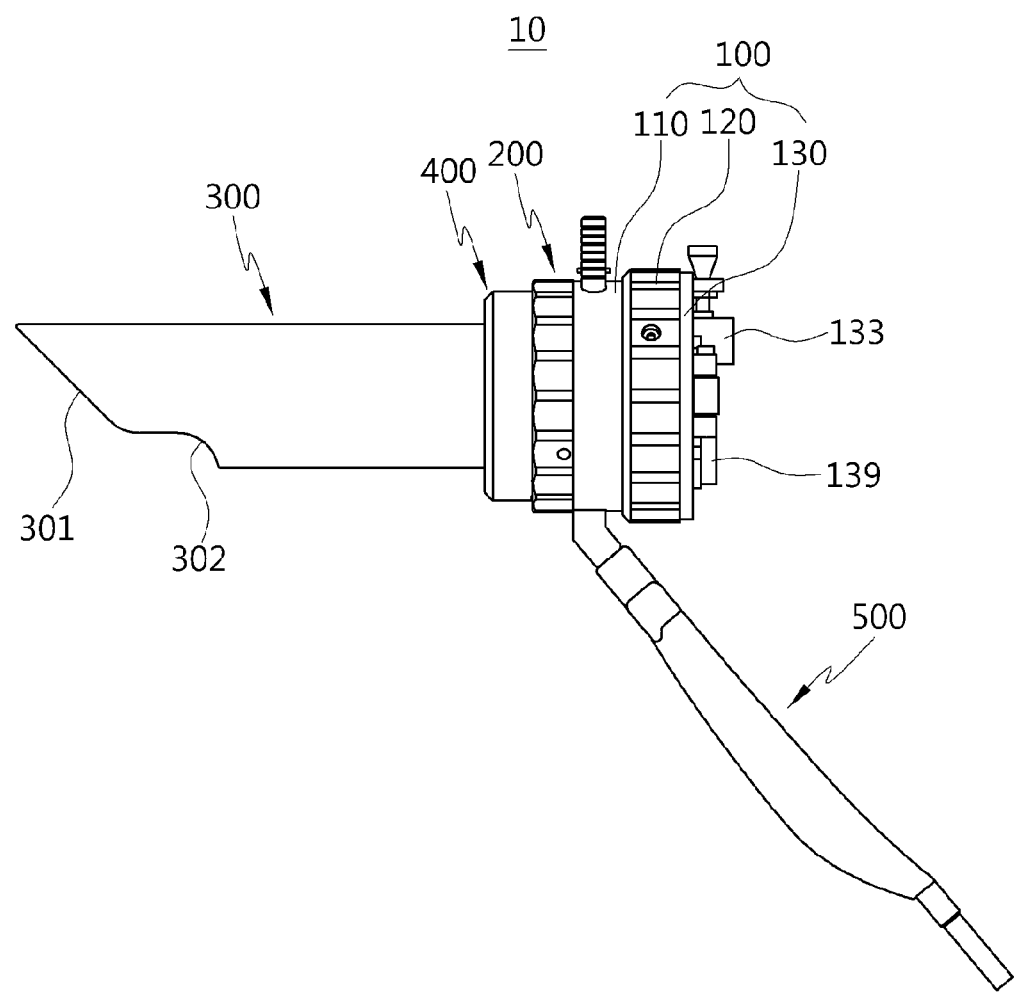
FIG. 3 is a side view of the surgical apparatus for TEM in accordance with an example embodiment of the present invention.

Hereinafter, example embodiments of the present invention will be described in detail. However, the present invention is not limited to the embodiments disclosed below, but can be implemented in various forms. The following embodiments are described in order to enable those of ordinary skill in the art to embody and practice the present invention. Like reference numerals designate like elements throughout the detailed description.

Hereinafter, a surgical instrument for TEM in accordance with an example embodiment of the present invention will be described with reference to the accompanying drawings. In the detailed description, if it is determined that description of conventional functions or constitutions may make the spirit of the invention unclear, detailed description thereof will be omitted.

Figure 4:
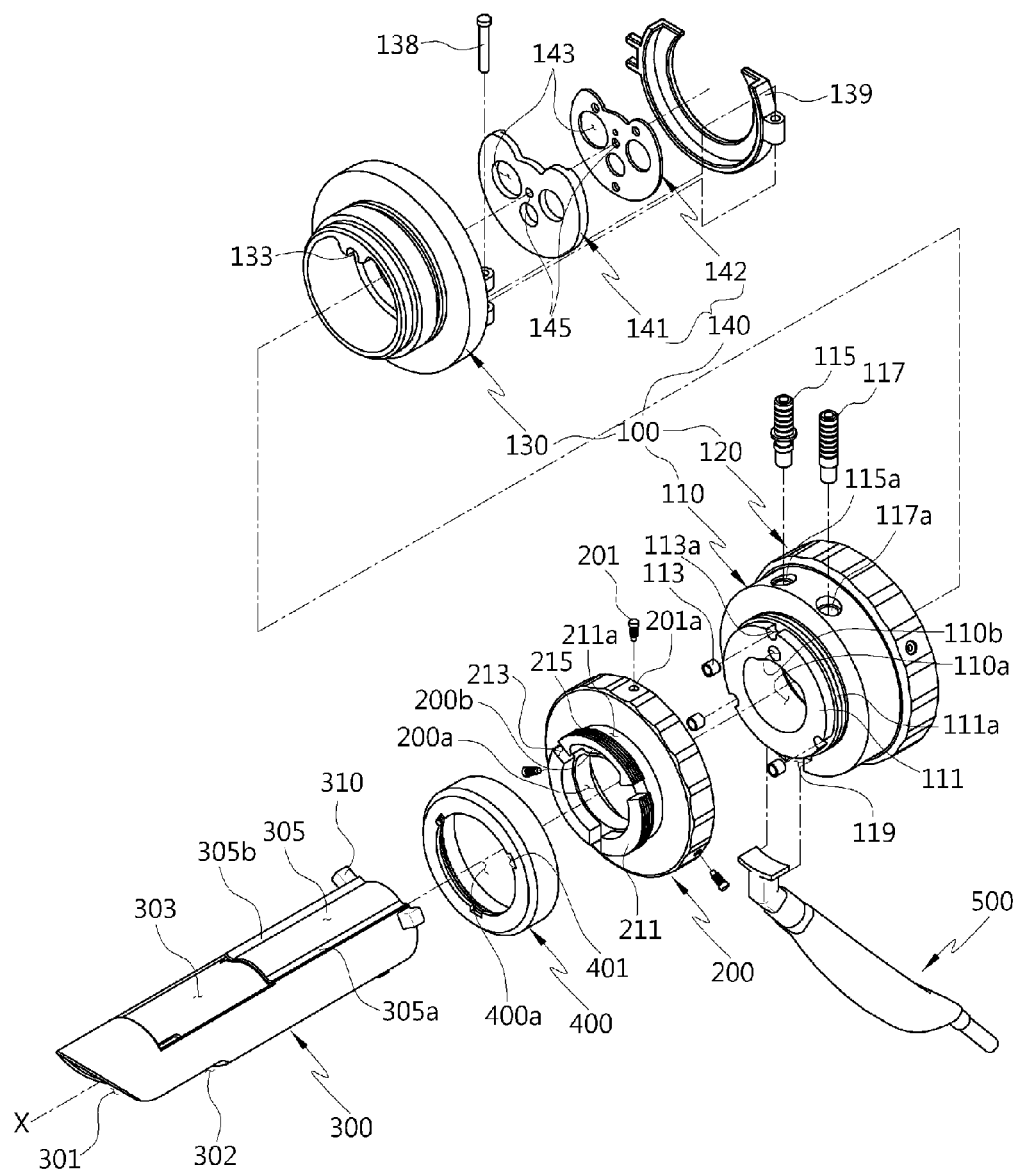
FIG. 4 is an exploded perspective view of surgical apparatus for TEM in accordance with an example embodiment of the present invention.
Figure 5:
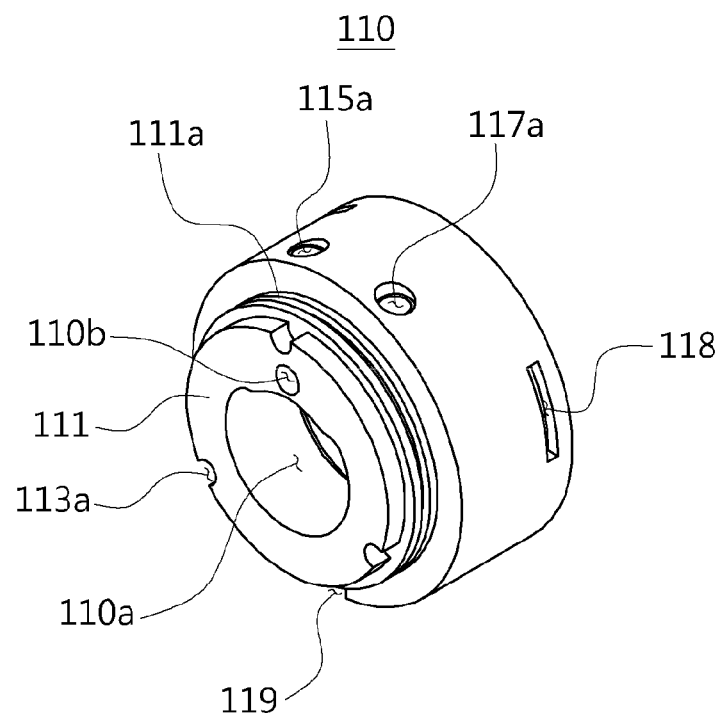
FIGS. 5 and 6 are front and rear perspective views of a housing, among components of a main body shown in FIG. 4.
Figure 6:
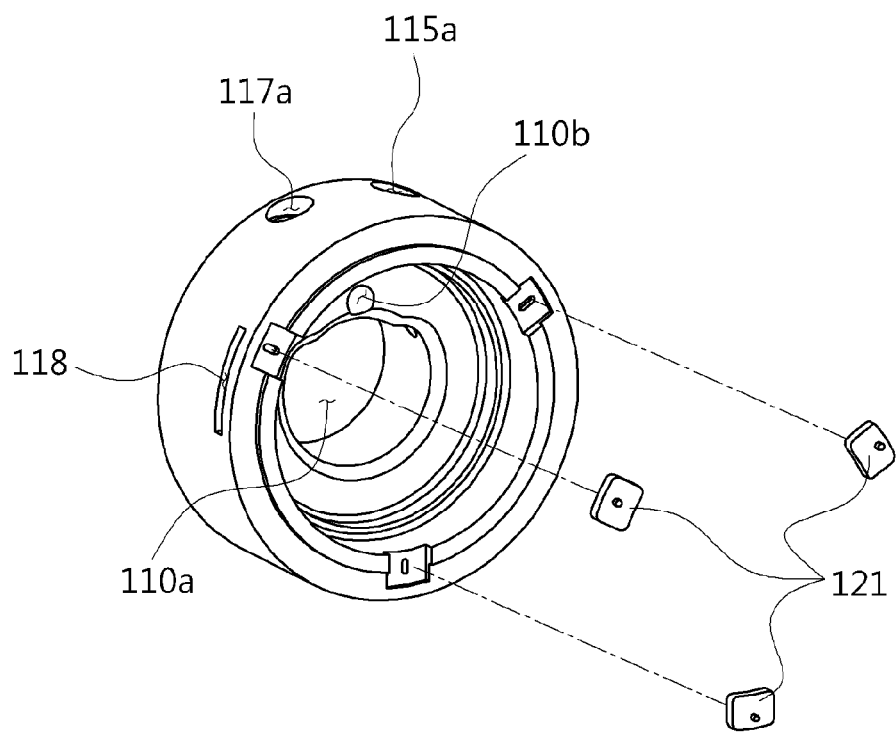
Figure 7:
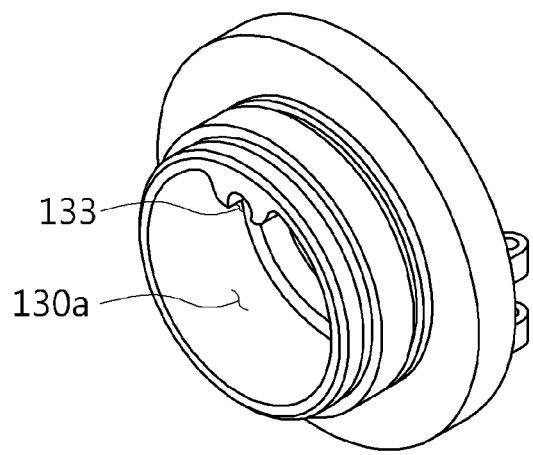
FIGS. 7 and 8 are front and rear perspective views of a tool insertion part, among the components of the main body shown in FIG. 4.
Figure 8:
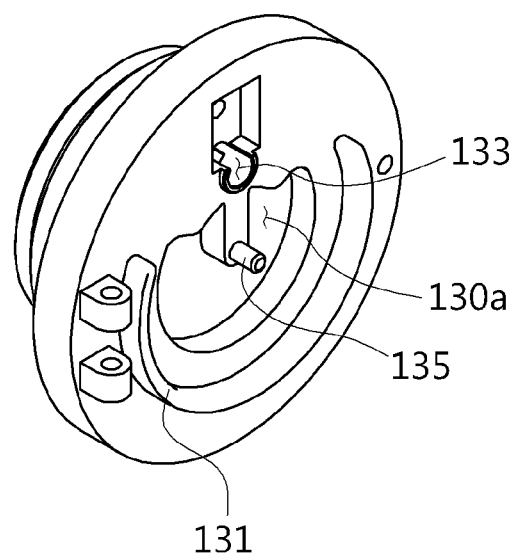
Figure 9:
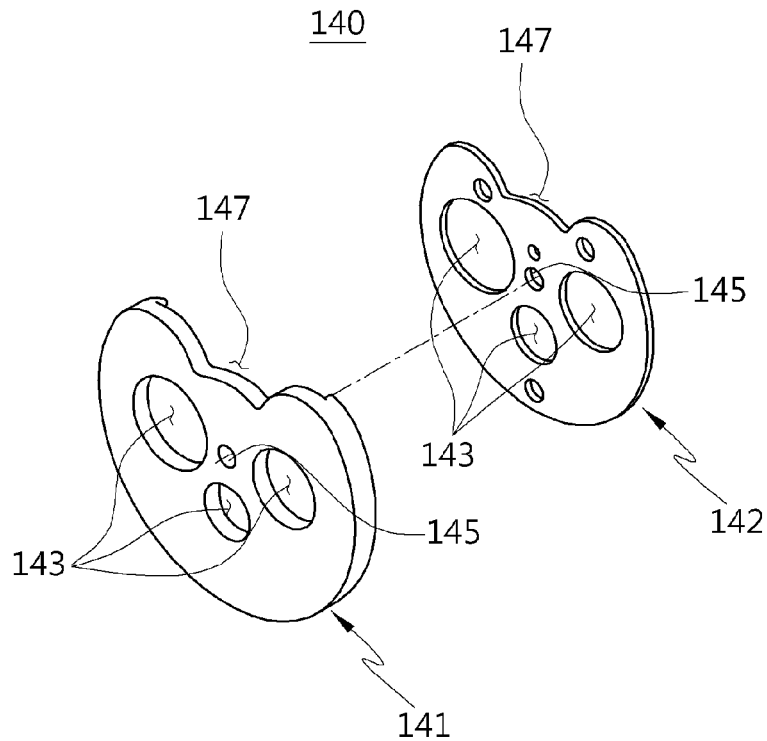
FIGS. 9 and 10 are front and rear perspective views of a surgical instrument insertion part, among the components of the main body shown in FIG. 4.
Figure 10:
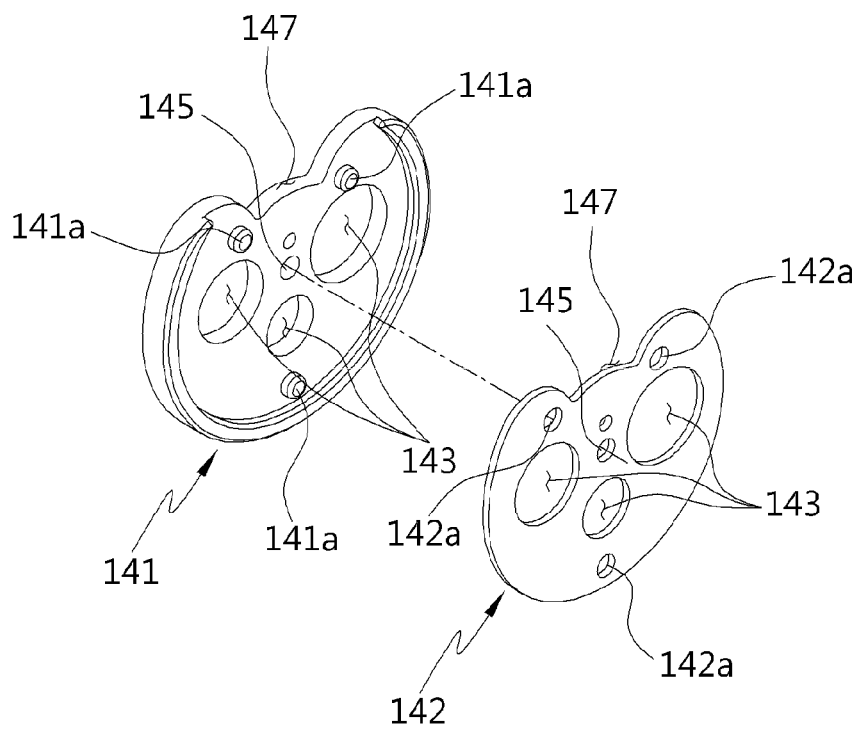
Figure 11:
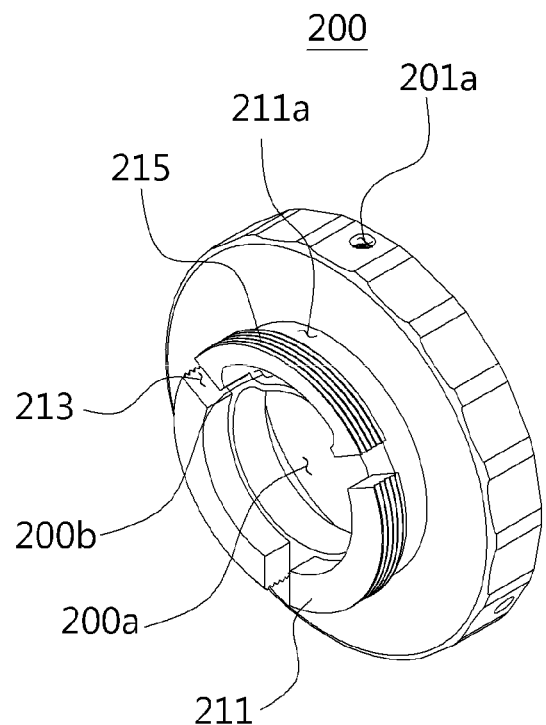
FIGS. 11 and 12 are front and rear perspective views of a rotary part shown in FIG. 4.
Figure 12:
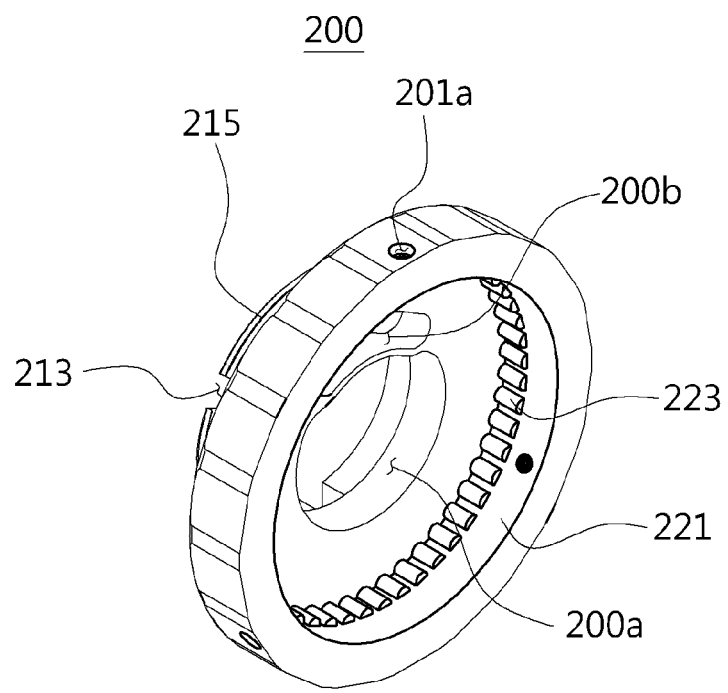
Figure 13:
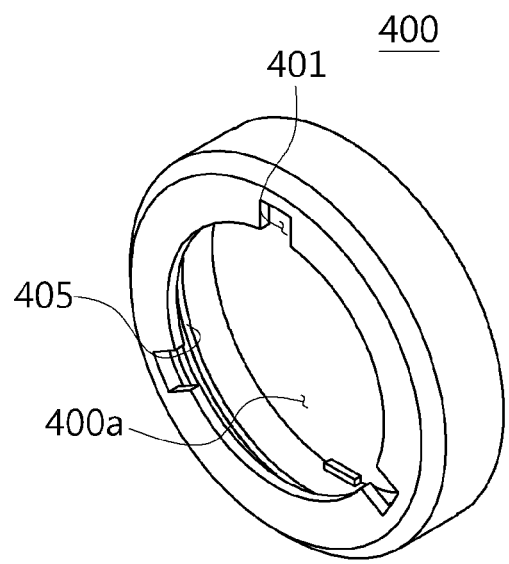
FIGS. 13 and 14 are front and rear perspective views of an example embodiment of a barrel fixing part shown in FIG. 4.
Figure 14:
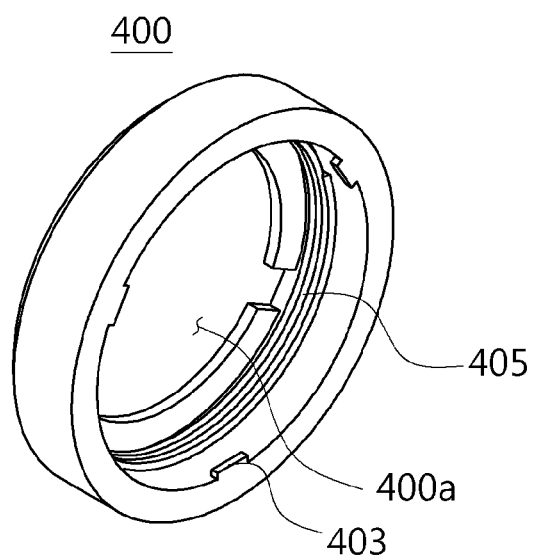
Figure 15:
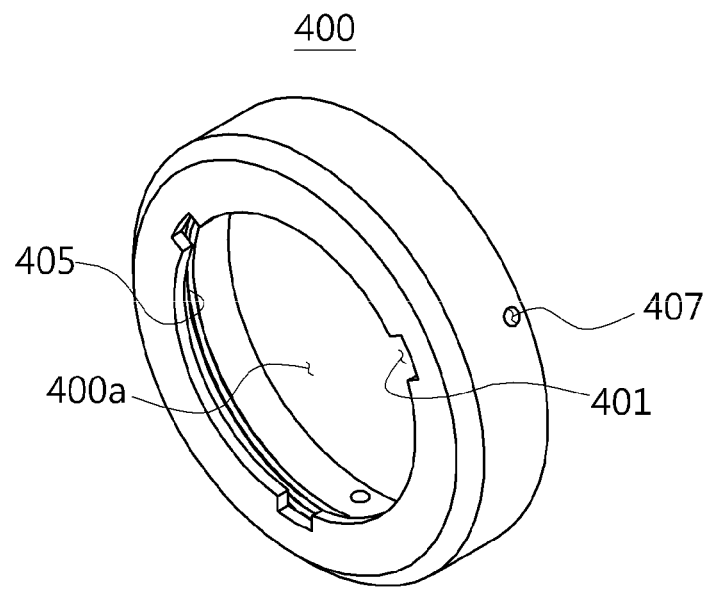
FIGS. 15 and 16 are front and rear perspective views of another example embodiment of the barrel fixing part.
Figure 16:
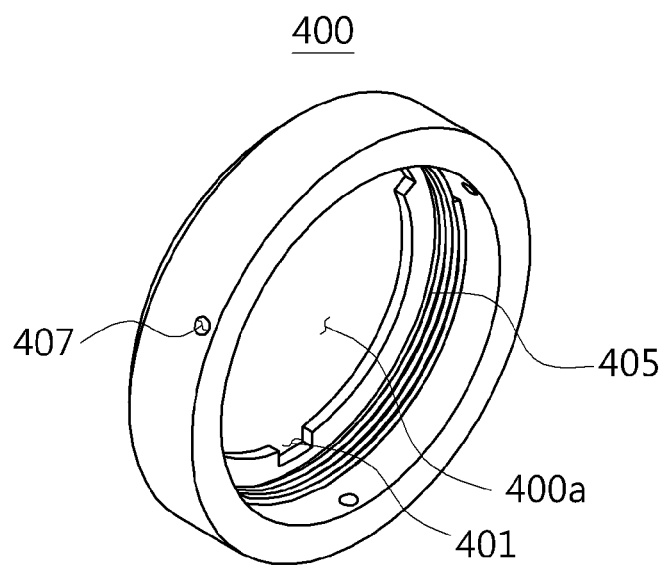
Figure 17:
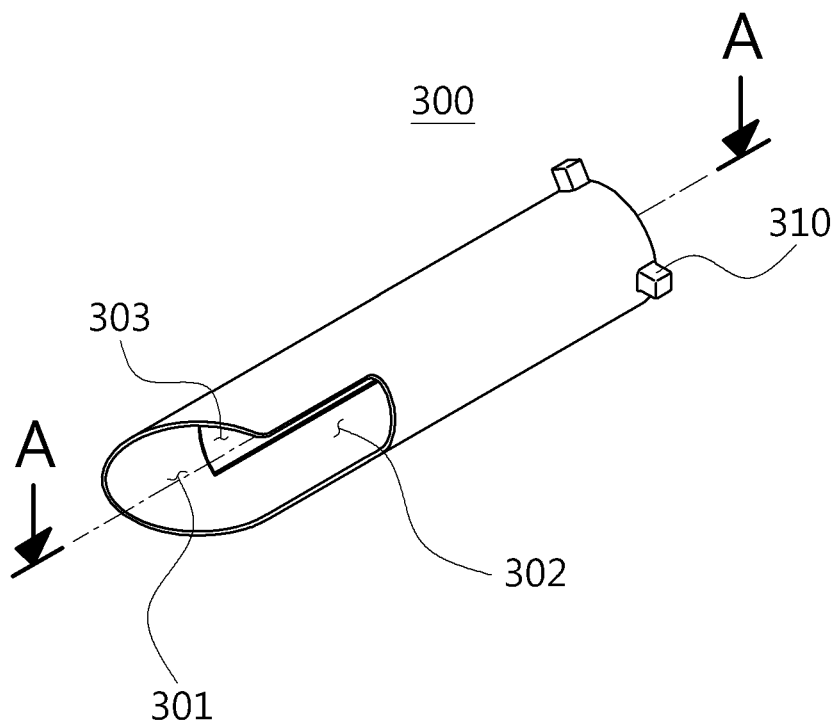
FIG. 17 is a perspective view of the barrel shown in FIG. 4, which is rotated to a certain angle.
Figure 18:
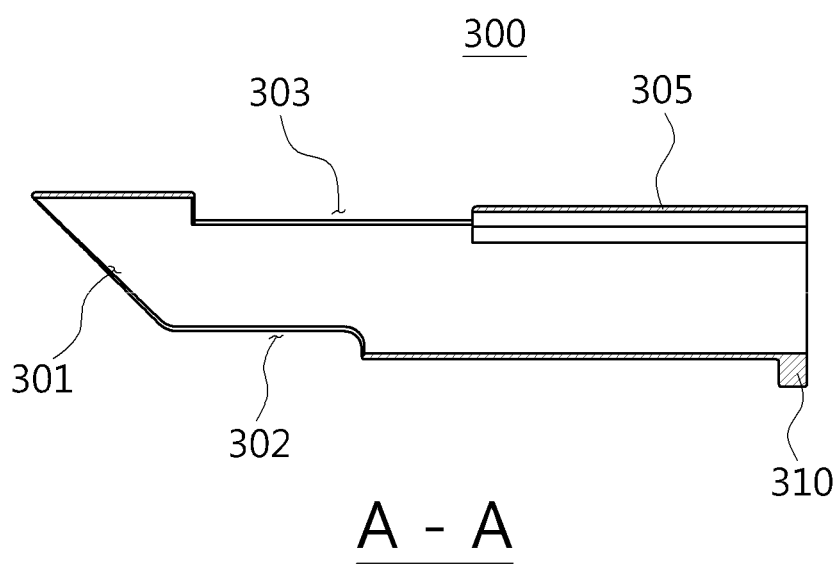
FIG. 18 is a cross-sectional view taken along line A-A of FIG. 7.
Figure 19:
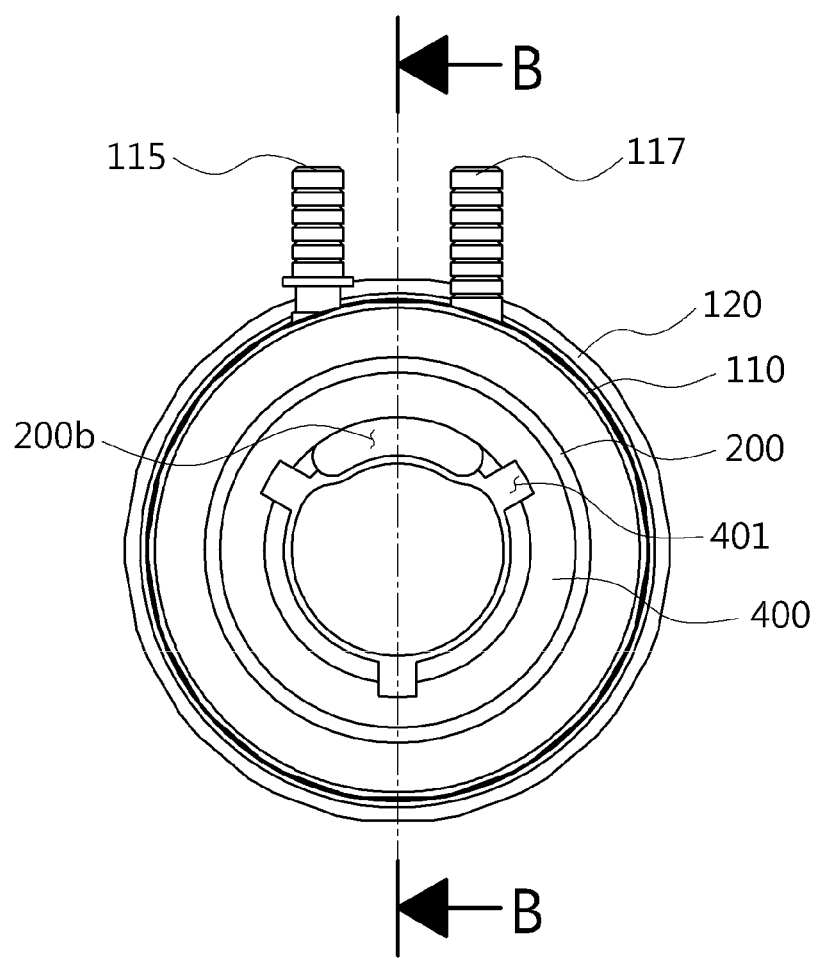
FIG. 19 is a front view showing an assembly of the main body, the rotary part and the barrel fixing part shown in FIG. 4.
Figure 20:
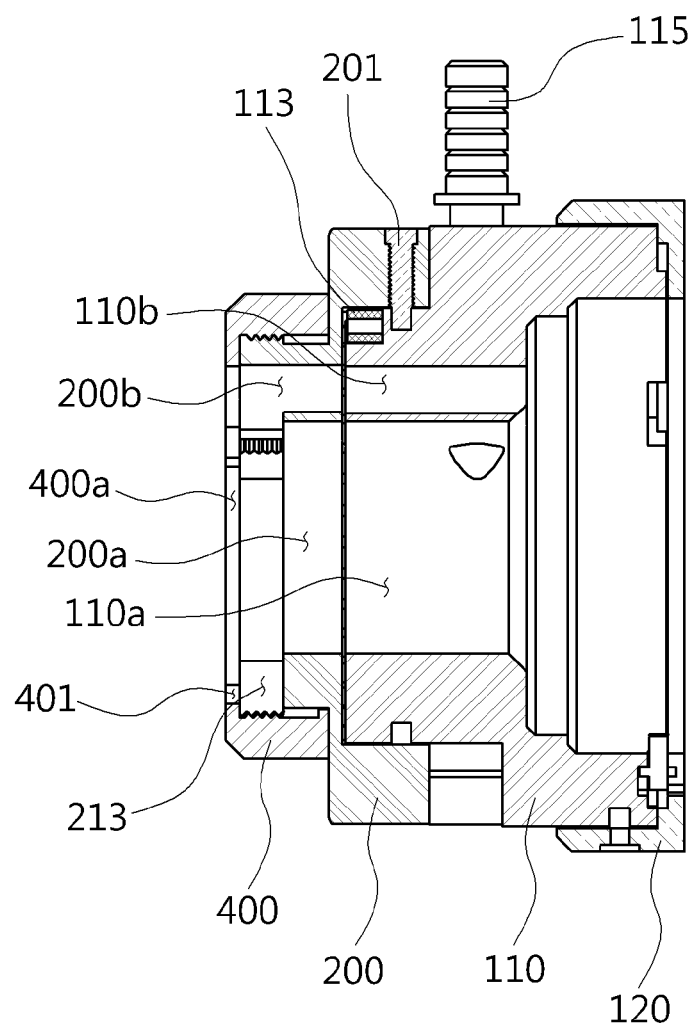
FIG. 20 is a cross-sectional view taken along line B-B of FIG. 19.
Figure 21:
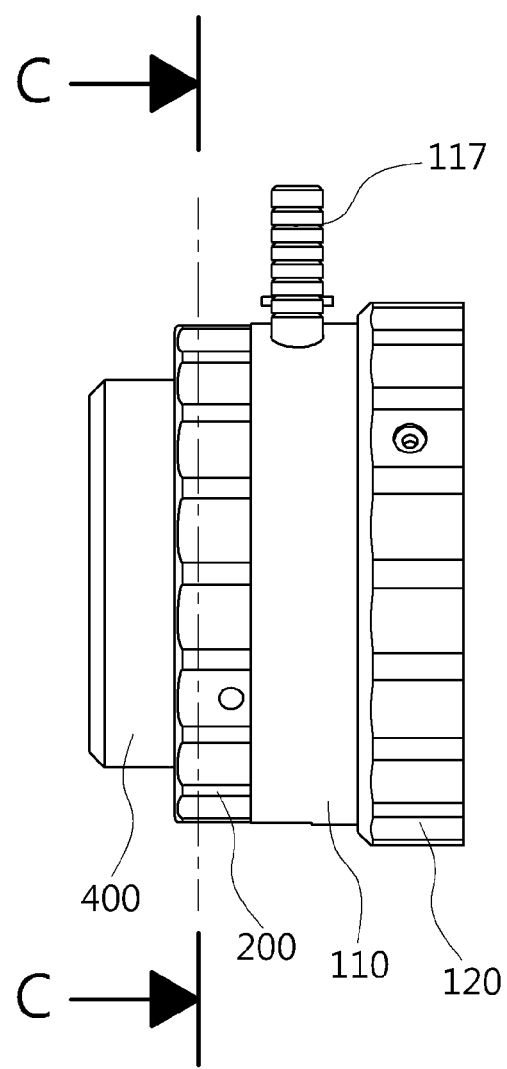
FIG. 21 is a side view of the assembly of the main body, the rotary part and the barrel fixing part shown in FIG. 4.
Figure 22:
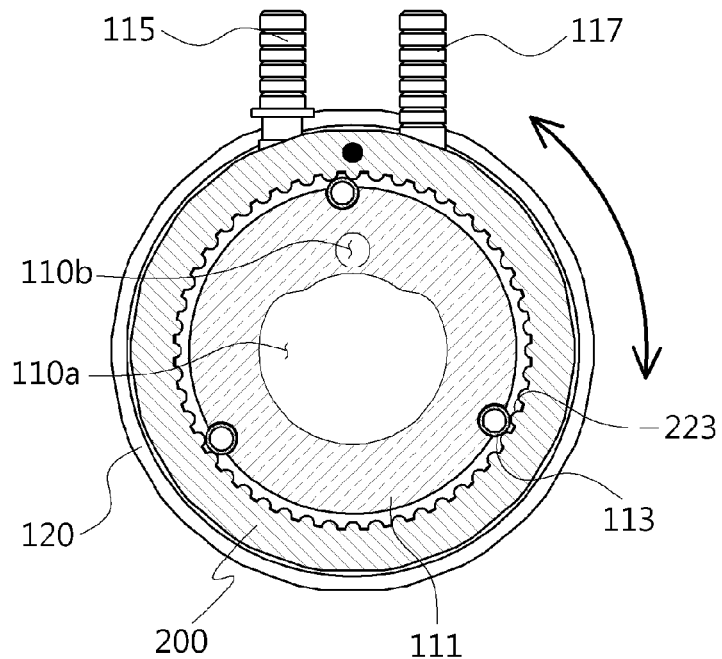
FIGS. 22 and 23 are cross-sectional views taken along line C-C of FIG. 21.
Figure 23:
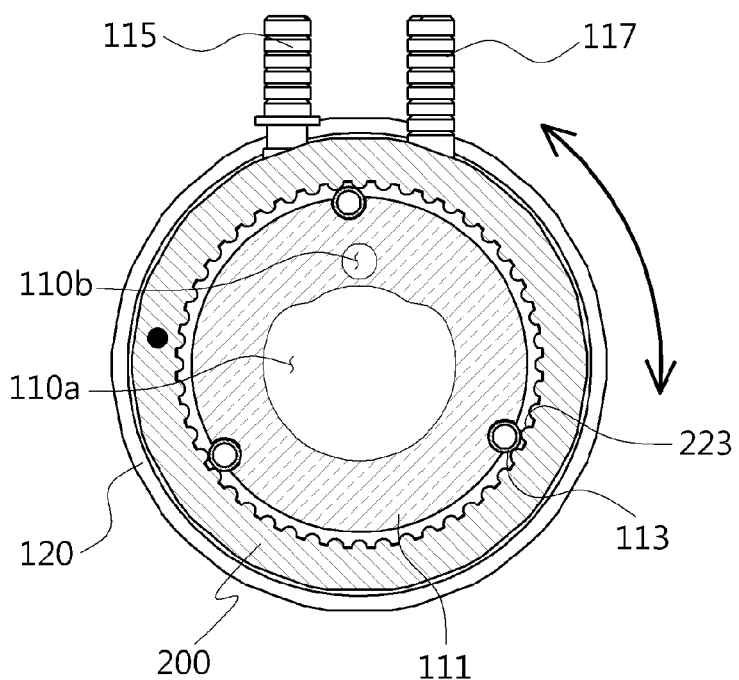

FIGS. 1 to 4 are front and rear perspective views, a side view and an exploded perspective view of a surgical apparatus for TEM in accordance with an example embodiment of the present invention FIGS. 5 and 6 are front and rear perspective views of a housing, among components of a main body shown in FIG. 4, FIGS. 7 and 8 are front and rear perspective views of a tool insertion part, among the components of the main body shown in FIG. 4, FIGS. 9 and 10 are front and rear perspective views of a surgical instrument insertion part, among the components of the main body shown in FIG. 4, FIGS. 11 and 12 are front and rear perspective views of a rotary part shown in FIG. 4, FIGS. 13 and 14 are front and rear perspective views of an example embodiment of a barrel fixing part shown in FIG. 4, FIGS. 15 and 16 are front and rear perspective views of another example embodiment of the barrel fixing part, FIG. 17 is a perspective view of the barrel shown in FIG. 4, which is rotated to a certain angle, FIG. 18 is a cross-sectional view taken along line A-A of FIG. 7, FIG. 19 is a front view showing an assembly of the main body, the rotary part and the barrel fixing part shown in FIG. 4, FIG. 20 is a cross-sectional view taken along line B-B of FIG. 19, FIG. 21 is a side view of the assembly of the main body, the rotary part and the barrel fixing part shown in FIG. 4, and FIGS. 22 and 23 are cross-sectional views taken along line C-C of FIG. 21, As shown in FIGS. 1 to 23, a surgical apparatus 10 for TEM in accordance with an example embodiment of the present invention includes a main body 100, a rotary part 200, a barrel 300, a barrel fixing part 400, and a main body supporter 500.

The main body 100 allows an endoscope 1 and various surgical instruments (not shown), which are provided for TEM, to be inserted thereinto.

The main body 100 includes an endoscope insertion port 133 into which the endoscope 1 is inserted, and surgical instrument insertion ports 143 into which various instruments (not shown) are inserted, respectively, wherein the surgical instrument insertion ports 143 are independently rotated from the endoscope insertion port 133.

The main body 100 includes a housing 110, a locking part 120, a tool insertion part 130, and a surgical instrument insertion part 140.

The housing 110 has a cylindrical shape through which the endoscope 1 and the various surgical instruments inserted through the tool insertion part 130 and the surgical instrument insertion part 140 can pass.

In addition, in order to prevent interference between the endoscope 1 and the various surgical instruments inserted into the housing 110, the housing 110 may have a surgical instrument through-hole 110a through which the various surgical instruments pass and an endoscope through-hole 110b through which the endoscope 1 passes, which are differentiated from each other. For example, the surgical instrument through-hole 11a may be formed at an inner center of the housing 110, and the endoscope through-hole 110b may be formed at an inner upper side of the housing 110, unlike the surgical instrument through-hole 110a.

The housing 110 has a coupling projection end 111 projecting from a front end of the housing 110 in a circular ring shape and having an outer diameter corresponding to an inner diameter of a rear end of the rotary part 200 such that the rotary part 200 is coupled to be axially rotated with respect to an X-axis (see FIG. 4). At least one first ring hole 113a is formed at the coupling projection end 111 such that the first ring 113 can be inserted as described below. While this embodiment illustrates the first ring 113 having a cylindrical shape to be rotatably inserted into the first ring hole 113a, the first ring 113 may have a spherical shape, not limited thereto. In addition, the first ring 113 is inserted into the first ring hole 113a to partially project therefrom to be engaged with a second ring 223.

In addition, an anti-separation groove 111a is formed at the coupling projection end 111 such that an anti-separation screw 210 is inserted along an outer periphery of a rear side of the first ring hole 113a to be hooked thereto, which will be described below.

At least one elongated hole 118, through which a screw (not shown) is inserted upon coupling to the locking part 120, is formed along an outer periphery thereof to limit a rotation angle of the locking part 120.

A gas discharge hole 115a may be formed at one side of an upper part of the housing 110 to receive a gas discharge pipe 115 to discharge an unnecessary internal gas, which may be generated during an operation, to the exterior. Here, a valve (not shown) may be installed at the gas discharge pipe 113 to adjust opening/closing of the gas discharge pipe 115.

In addition, a gas injection pipe 117a may be formed at the other side of the upper part of the housing 110 to receive a gas injection pipe 117 to inject an external gas needed upon the operation, for example, $CO_2$ gas, to the operation area.

A supporter fixing hole 119 is formed at a lower part of the housing 110 to fix a main body supporter 500, which will be described below.

The locking part 120 is disposed between the housing 110 and the tool insertion part 130 to lock the tool insertion part 130 into the housing 110.

The locking part 120 has a circular ring shape and is rotatably locked to the rear end of the housing 110. For example, the housing 110 includes lock protrusions 121 movable in a radial direction thereof, and the locking part 120 has rock grooves (not shown) having radiuses that vary in a rotation direction of the locking part 120 to receive the lock protrusions 121. Therefore, when the locking part 120 is rotated clockwise or counterclockwise with respect to the housing 110, the lock protrusions 121 move along the lock grooves in a radial direction to lock or unlock the lock protrusions 121 and the lock grooves, rotatably locking or unlocking the locking part 120 from the housing 110. This locking structure may be understood as a conventional technique, and thus, detailed description thereof will be omitted. In addition, while the embodiment illustrates the lock protrusions 121 and the rock grooves, various locking structures may be used, not limited thereto.

The tool insertion part 130 is inserted from the rear part of the locking part 120 and coupled thereto.

The tool insertion part 130 may have an endoscope insertion port 133 into which the endoscope is inserted, and a surgical instrument through-hole 130a through which various surgical instruments inserted through a surgical instrument insertion port 143 of the surgical instrument insertion part 140 pass. For example, the surgical instrument through-hole 130a may be formed through a center of the interior of the tool insertion part 130, and the endoscope insertion port 133 may be formed at an upper side of the interior of the tool insertion part 130, separately from the surgical instrument through-hole 130a. Here, the endoscope insertion port 133 of the tool insertion part 130 is correspondingly in communication with the endoscope through-hole 110b of the housing 110, and the endoscope 1 is disposed outside the barrel 300 such that a visual field of the endoscope 1 is uniformly disposed outside the outer diameter of the barrel 300 even when the barrel 300 is rotated. In addition, an elastic member such as silicon rubber (not shown) may be provided along an inner diameter of the endoscope insertion port 133 to elastically support the endoscope 1 inserted through the endoscope insertion port 133. Further, the surgical instrument through-hole 130a of the tool insertion part 130 may be correspondingly in communication with the surgical instrument through-hole 110a of the housing 110, and may be opened around a rotary shaft protrusion 135 to include a lateral rotation angle range of the surgical instrument insertion port 143 of the surgical instrument insertion port 140.

In addition, the rotary shaft protrusion 135 may be formed at a center of the rear surface of the tool insertion part 130 to be inserted into a rotary shaft groove 145 of the surgical instrument insertion part 140 so that the surgical instrument insertion part 140 can be laterally and rotatably movably coupled to the tool insertion part 130.

Further, the tool insertion part 130 may include a rotation guide member 131 to rotatably guide the surgical instrument insertion part 140. For example, the rotation guide member 131 projects from the rear surface of the tool insertion part 130 to form a semi-circular rib shape, an upper part of which is open along an outer periphery of the surgical instrument through-hole 130a about the rotary shaft protrusion 135 to support the outer periphery of the surgical instrument insertion part 140 to be rotatably guided. While the embodiment illustrates the rotation guide member 131 having the semi-circular rib shape, the rotation guide member 131 may include various shapes that can rotatably guide the surgical instrument insertion part 140, not limited thereto.

Furthermore, a tool insertion cover 139 may be rotatably coupled to the tool insertion part 130 by a hinge pin 138 to prevent separation of the surgical instrument insertion part 140 supported by the rotation guide member 131.

The surgical instrument insertion part 140 is rotatably installed at the rotary shaft protrusion 135 of the tool insertion part 130. For example, the surgical instrument insertion part 140 may have a rotary shaft groove 145, into which the rotary shaft protrusion 135 of the tool insertion part 130 is rotatably inserted, such that the surgical instrument insertion part 140 is laterally rotatably coupled to the tool insertion part 140. The surgical instrument insertion part 140 may be constituted by a main insertion body 141 inserted into the rotation guide member 131 to be rotatably guided, and an auxiliary insertion body 142 detachably coupled to the main insertion body 141. While the embodiment illustrates the surgical instrument insertion part 140 constituted by the main insertion body 141 and the auxiliary insertion body 142, which have a coupling protrusion 141a and coupling grooves 142a, respectively, to be fastened to each other, the main insertion body 141 may be integrally formed with the auxiliary insertion body 142, not limited thereto.

In addition, the surgical instrument insertion port 143 is formed at the surgical instrument insertion part 140 to receive various surgical instruments for TEM. At least one surgical instrument insertion port 143 may be formed around the rotary shaft groove 145, and may have various shapes such as a circular or polygonal shape, etc. For example, while the embodiment illustrates the surgical instrument insertion port 143 having three circular holes with different diameters around the rotary shaft groove 145, the surgical instrument insertion port 143 may have a single hole, two holes, or four holes or more, diameters of which may be equal to or different from each other. Here, an elastic member such as silicon rubber (not shown) may be provided along an inner diameter of the surgical instrument insertion port 143 to elastically support the various surgical instruments inserted through the surgical instrument insertion port 143.

Further, the surgical instrument insertion part 140 may have an anti-interference groove 147 formed at an upper edge of the surgical instrument insertion part 140 opposite to the endoscope 1 and corresponding to a lateral rotation angle range of the surgical instrument insertion part 140 to prevent interference with the endoscope 1 inserted through the endoscope insertion port 133 when the surgical instrument insertion part 140 is laterally rotated about the rotary shaft protrusion 135 of the tool insertion part 130. Here, a projection (not shown) may project around the endoscope insertion part 133 to limit the rotation of the surgical instrument insertion part 140 using the projection hooked by the anti-interference groove 147. In addition, the projection prevents direct contact between the endoscope 1 and the anti-interference groove 147 to prevent damage to or shaking of the endoscope 1. The anti-interference groove 147 may have a size appropriate to the lateral rotation angle range of the surgical instrument insertion part 140 about the rotary shaft protrusion 135 of the tool insertion part 130. For example, when the surgical instrument insertion part 140 can be laterally rotated within a range of ±25° about the rotary shaft protrusion 135 of the tool insertion part 130, the anti-interference groove 147 may have the entire rotation angle of 50°.

The rotary part 200 has a substantially cylindrical shape through which the endoscope 1 and the various surgical instruments inserted into the main body 100 pass.

In addition, in order to prevent interference between the endoscope 1 and the various surgical instruments passing through the rotary part 200, the rotary part 200 may be configured to differentiate a surgical instrument through-hole 200a, through which the surgical instruments pass, from an endoscope through-hole 200b, through which the endoscope 1 passes. For example, the surgical instrument through-hole 200a may be formed at an inner center of the rotary part 200 to be correspondingly in communication with the surgical instrument through-hole 110a, and the endoscope through-hole 200b may be formed at an inner upper side of the rotary part 200, separately from the surgical instrument through-hole 200a. Here, the endoscope through-hole 200b of the rotary part 200 is correspondingly in communication with the endoscope through-hole 110b of the housing 110, such that the endoscope 1 passes therethrough to be disposed outside the barrel 200. Further, the endoscope through-hole 200b of the rotary part 200 may have an elongated hole formed along a circumference thereof to a rotation angle including a lateral rotation range of the rotary part 200 such that the rotary part 200 can be laterally moved without any interference in a state in which the endoscope 1 passes therethrough.

The rotary part 200 is axially rotatably coupled to the front end of the main body 100 with respect to an X-axis. More specifically, a coupling groove end 221 is formed at the rear end of the rotary part 200 and has an inner diameter corresponding to an outer diameter of the coupling projection end 111 of the housing 110, and the coupling projection end 111 is inserted into the coupling groove end 221 such that the rotary part 200 can be rotatably coupled to the housing 110.

In order to uniformly adjust a rotation angle of the rotary part 200 in a stepped manner when the rotary part 200 is rotated with respect to the main body 100, a rotation angle adjustment unit may be installed between the main body 100 and the rotary part 200. For example, the rotation angle adjustment unit may include at least one first ring 113 installed at an outer periphery of the coupling projection end 111 of the housing 110, and a plurality of second rings 223 installed along an inner periphery of the coupling groove end 221 of the rotary part 200 at predetermined intervals. Therefore, when the rotary part 200 is rotated with respect to the main body 100, the first ring 113 is in contact with the second rings 223 in the rotation direction in a stepped manner to uniformly adjust the rotation angle of the rotary part 200, improving click feeling of the rotation. Here, three first rings 113 having a cylindrical shape may be formed at the outer periphery of the coupling projection end 111 of the housing 110 at predetermined angular intervals, for example, 120°, and the plurality of second rings 223 having a semi-cylindrical shape may be installed at the inner periphery of the coupling groove end 221 of the rotary part 200. While the embodiment illustrates a constitution that the first ring 113 is a cylindrical rotary ring and the second ring 223 is a semi-cylindrical fixed ring, it will be sufficient that at least one of the first ring 113 and the second ring 223 may be a rotary ring, not limited thereto. As shown in FIGS. 20 and 21, when the rotary part 200 is rotated with respect to the housing 110, the first ring 113 of the housing 110 is rotated in a normal position, and the second ring 223 is in contact with the first ring 113 to be rotated with rotation of the rotary part 200.

Figure 24:
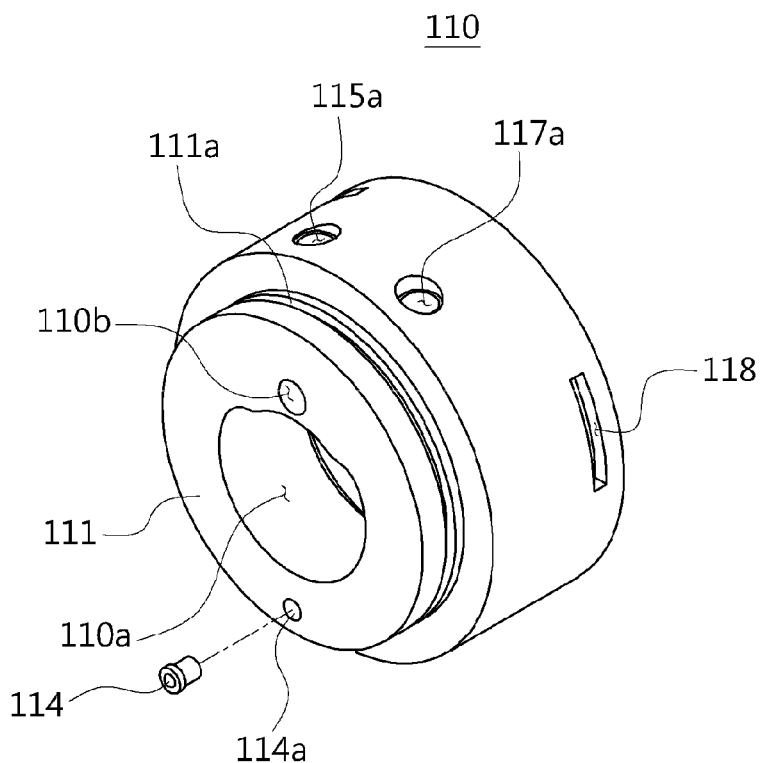
FIG. 24 is a perspective view of a housing for explaining another embodiment of a rotation angle adjustment unit.
Figure 25:
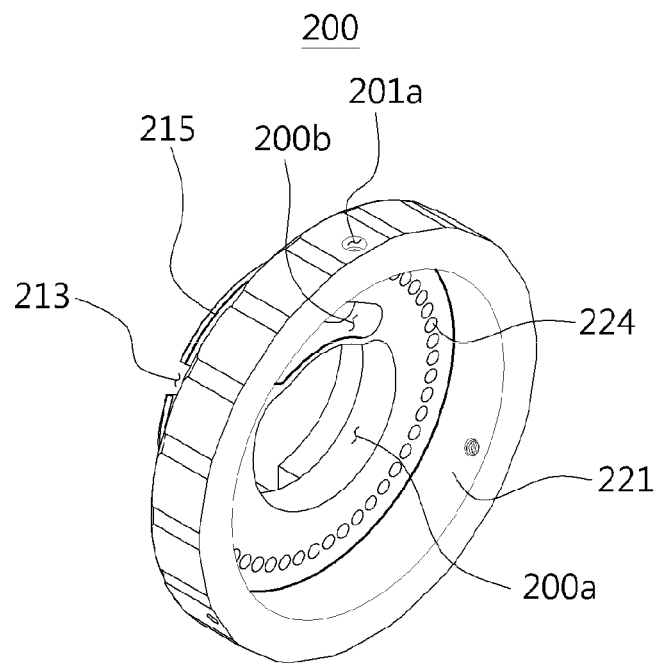
FIG. 25 is a perspective view of a rotary part for explaining another embodiment of the rotation angle adjustment unit.
Figure 26:
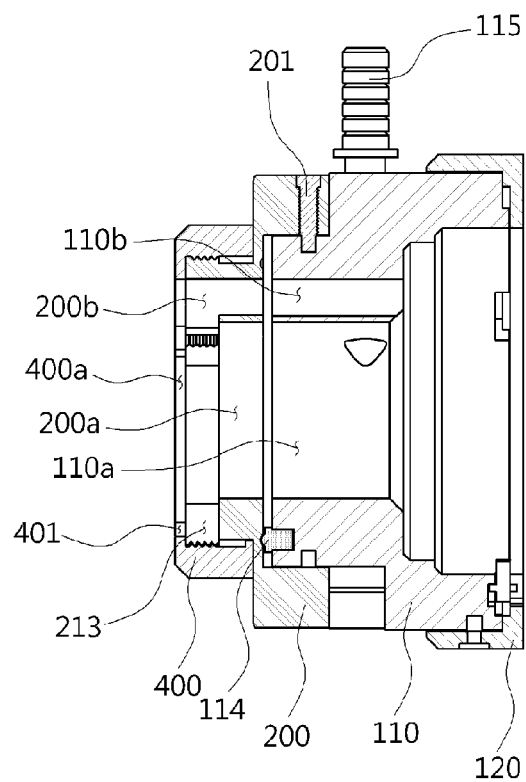
FIG. 26 is a cross-sectional view of an assembly of a housing, a rotary part and a barrel fixing part shown in FIGS. 24 and 25.

In addition, while the embodiment illustrates the rotation angle adjustment unit having two rings 113 and 223 engaged with each other, various embodiments may be employed, not limited thereto. For example, as shown in FIGS. 22 to 24, the rotation angle adjustment unit includes at least one click ball 114 inserted into a hole 114a formed at a lower part of a front surface of the coupling projection end 111 of the housing 110 and resiliently supported by a spring (not shown), and a plurality of semi-spherical click grooves 224 formed at a rear surface of the coupling groove end 221 of the rotary part 200 at predetermined intervals, such that the click ball 114 is inserted into the click grooves 224 in a stepped manner to rotate the rotary part 200 to a certain angle with respect to the main body 100. Here, the click ball 114 may have various shapes, for example, the click ball 114 may have a cylindrical ball body and the ball body may have a semi-spherical end projecting from its front surface to correspond to the click groove 224.

Further, in order to prevent separation of the rotary part 200 from the main body, an anti-separation unit may be installed between the main body 100 and the rotary part 200. For example, the anti-separation unit may include an anti-separation groove 111a formed along an outer periphery of the coupling projection end 111 of the housing 110, and an anti-separation screw 210 inserted through a screw hole 201a formed at the rotary part 200 corresponding to the anti-separation groove 111a to be hooked by the anti-separation groove 111a to rotatably guided. While the embodiment illustrates a constitution in which the anti-separation screw 210 is hooked by the anti-separation groove 111a to prevent separation of the rotary part 200 from the main body 100, an anti-separation protrusion (not shown) having a projection rib shape such as the anti-separation protrusion 403 of the barrel fixing part 400 may be formed at an inner diameter of the coupling groove end 221 of the rotary part 200 to be detachably coupled to the anti-separation groove 111a of the housing 110, not limited thereto.

A fixed projection end 211 having an outer diameter corresponding to an inner diameter of the rear end of the barrel fixing part 400 and projecting in a circular ring shape is formed at the front end of the rotary part 200. Fixing holes 213, into which fixing protrusions 310 of the barrel 300 are inserted, respectively, are correspondingly formed at the fixing projection end 211. In addition, a male screw 215 may be formed at an outer periphery of the fixing projection end 211 to be threadedly engaged with a female screw 495 formed at an inner periphery of the barrel fixing part 400.

Further, an anti-separation groove 211a is formed at the fixing projection end 211 such that an anti-separation protrusion 403 of the barrel fixing part 400 is inserted along an outer periphery of a rear side of the male screw 215 to be hooked thereto.

The barrel 300 may have an elongated cylindrical shape, which can be inserted into the patient's anus, to provide a guide path of the endoscope and the various surgical instruments inserted through the main body 100.

The barrel 300 is fixed to the front end of the rotary part 200 to be integrally rotated with rotation of the rotary part 200. More specifically, the rear end of the barrel 300 is inserted into the fixing projection end 211 of the rotary part 200, and the fixing protrusion 310 of the barrel 300 is inserted and fixed into a fixing hole 213 of the rotary part 200. That is, at least two fixing protrusions 310 may be formed at the rear end of the barrel 300 to be inserted into the fixing hole 213 of the fixing projection end 211 of the rotary part 200.

The barrel 300 may have an inclined opening surface 301 inclined about 45° with respect to a longitudinal direction of the barrel 300 at its tip. In addition, the barrel 300 may include an enlarged opening surface 302 extending from a lower part of the inclined opening surface 301 and enlarging a lower opening area. That is, the enlarged opening surface 302 may be further enlarged rearward from the lower part of the inclined opening surface 301 in a stepped manner. As a result of formation of the enlarged opening surface 302 at the tip of the barrel 300, the diameter of the barrel may be reduced from 40 mm to 30 mm according to a patient's body type to enlarge a movement range of the various surgical instruments and the endoscope 1.

According to the present invention, the endoscope inserted through the endoscope insertion port 133 of the main body 100 and passing through the endoscope through-hole 200b of the rotary part 200 is disposed outside the barrel 300, and the surgical instruments inserted through the surgical instrument insertion port 143 of the main body 100 and passing through the surgical instrument through-hole 200a of the rotary part 200 are disposed inside the barrel 300. For this purpose, the barrel 300 includes an endoscope opening surface 303 formed to correspond to the tip of the endoscope 1 disposed outside of an upper side of the barrel. Here, the tip of the endoscope 1 may be bent at a predetermined angle, for example, about 30°, toward the inclined opening surface 310 through the endoscope opening surface 303. In addition, an endoscope guide groove 305 having a circular cross-section with a reduced outer diameter of the barrel 300 corresponding to the endoscope through-hole 200b of the rotary part 200 formed at the upper surface of the barrel 300 from a rear end of the barrel 300 to a rear end of the endoscope opening surface 303 in a longitudinal direction of the barrel 300 such that the endoscope 1 passes through the endoscope through-hole 200b of the rotary part 200 is disposed outside of the upper side of the barrel 300. Further, semi-spherical grooves 305a and 305b may be formed at left and right sides of the endoscope guide groove 305 to limit a lateral rotation angle range of the barrel 300 through contacts with the endoscope 1. As a result of disposition of the endoscope outside the barrel 300 and the various surgical instruments inside the barrel 300, it is possible to prevent interference between the endoscope 1 and the various surgical instruments and reduce the outer diameter of the barrel 300 to minimize probability of injury to the patient's anus.

The barrel fixing part 400 has a barrel insertion hole 400a formed at its center to receive the barrel 300, and the barrel insertion hole 400a has a through-hole 401 formed to correspond to the fixing protrusion 310 such that the fixing protrusion 310 of the barrel 300 can pass. Therefore, the barrel fixing part 400 has a generally circular-ring shape.

The barrel fixing part 400 is coupled to the front end of the rotary part 200 to fix the barrel 300 to the rotary part 200. For example, the barrel fixing part 400 is threadedly engaged with the rotary part 200 to fix the barrel 300 to the rotary part 200 in a state in which the barrel 300 is inserted thereinto. For this purpose, a female thread 405 may be formed at an inner periphery of the barrel fixing part 400 to be threadedly engaged with the male thread 215 of the rotary part 200.

As shown in FIGS. 13 and 14, in accordance with an example embodiment of the present invention, the anti-separation protrusion 403 having a rib shape is formed at an inner periphery of the rear end of the barrel fixing part 400 to correspond to the fixing hole 213 of the rotary part 200 to be inserted into the anti-separation groove 211a of the rotary part 200, preventing separation of the barrel fixing part 400 from the rotary part 200. Otherwise, as shown in FIGS. 15 and 16, in accordance with another example embodiment of the present invention, the anti-separation screw (not shown) is inserted through at least one screw hole 407 formed at an outer periphery of the barrel fixing part 400 to be hooked by the anti-separation groove 211a of the rotary part 200 to guide rotation thereof, preventing separation of the barrel fixing part 400 from the rotary part 200.

The main body supporter 500 may be detachably coupled to a lower part of the housing 110 to support the surgical apparatus 10 for TEM upon the operation.

FIGS. 27 to 39 are views for sequentially explaining assembly processes and operations of the surgical apparatus for TEM.

Figure 27:
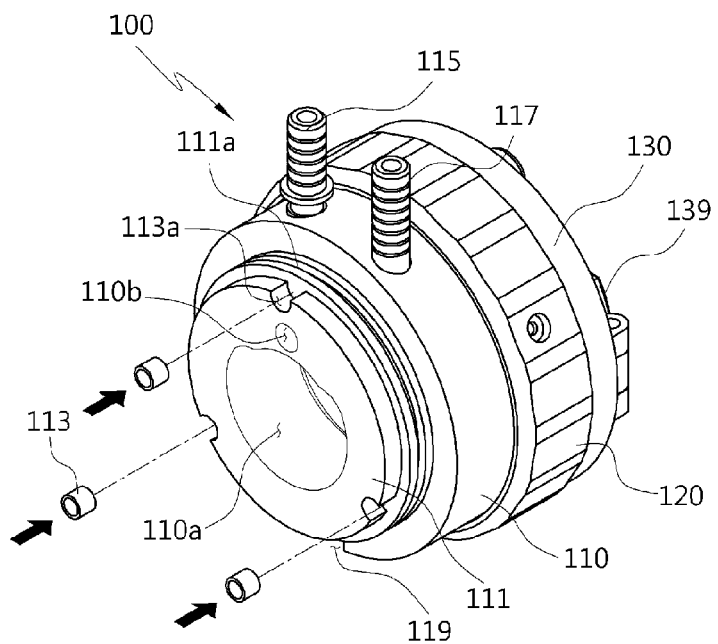
FIGS. 27 to 39 are views for sequentially explaining assembly processes and operations of the surgical apparatus for TEM.

First, as shown in FIG. 27, a housing 110, a locking part 120, and a tool insertion part 130 are coupled to assemble a main body 100. In addition, first rings 113 are inserted into first ring holes 113a formed at a coupling projection end 111 of the housing 110, a gas discharge pipe 115 is inserted into a gas discharge hole 115a, and a gas injection pipe 117 is inserted into a gas injection hole 117a.

Figure 28:
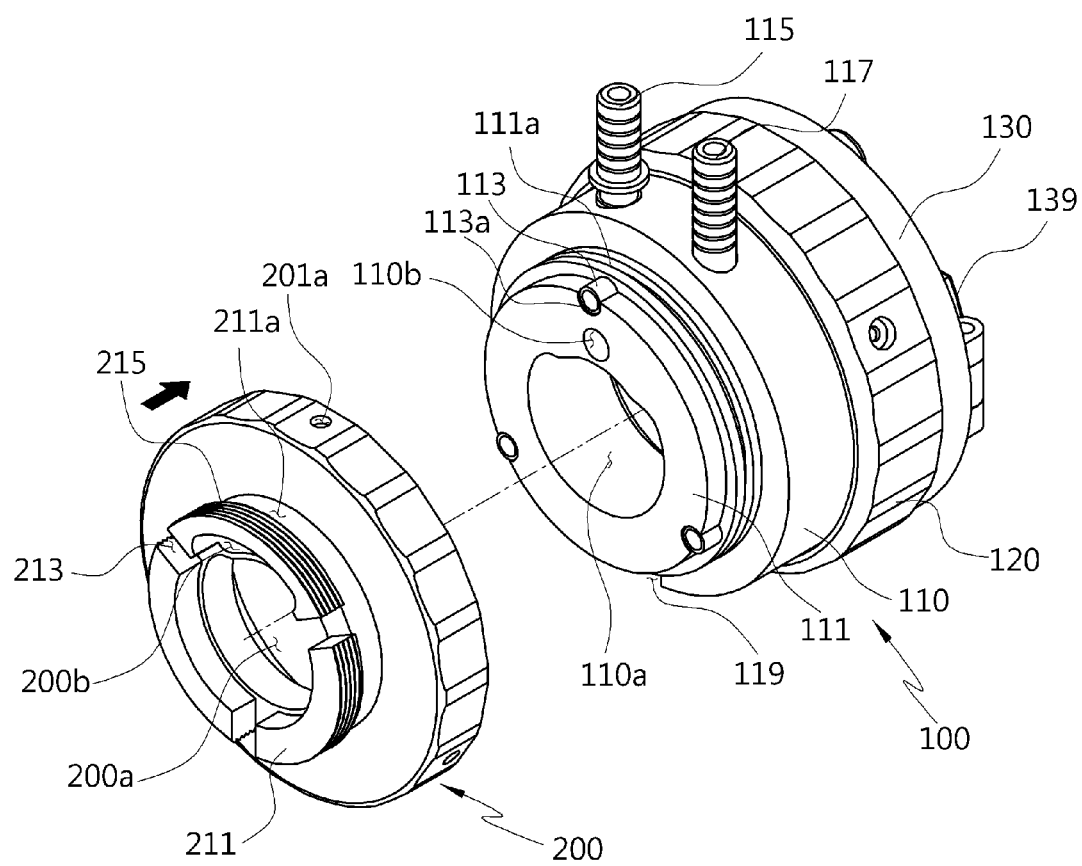

Next, as shown in FIG. 28, the coupling projection end 111 of the housing 110 is inserted into a coupling groove end 221 of the rotary part 200 to rotatably assemble the rotary part 200 to the housing 110. Here, the first ring 113 installed at the coupling projection end 111 of the housing 110 is engaged with a second ring 223 installed at the coupling groove end 221 of the rotary part 200 to be in contact therewith.

Figure 29:
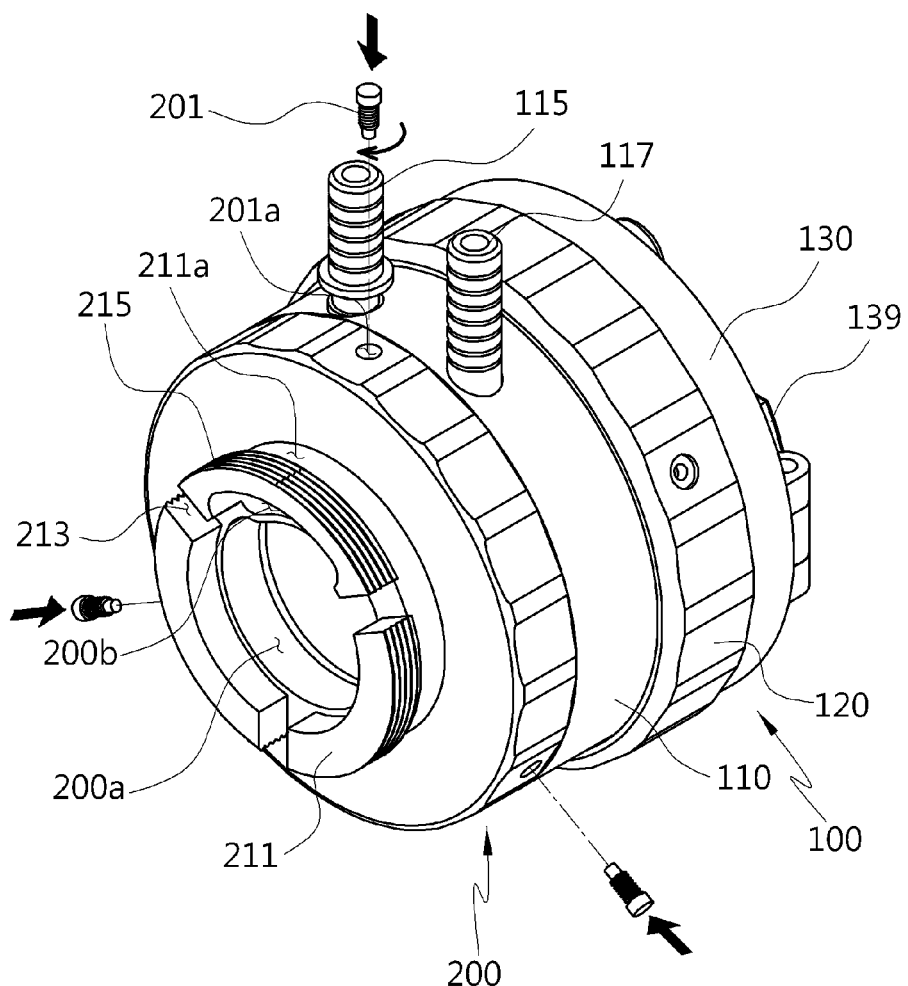

Then, as shown in FIG. 29, a screw 201 is fastened to a screw hole 201a of the rotary part 200 such that the screw 201 is inserted into and hooked by the anti-separation groove 111a formed at the coupling projection end 111 of the housing 110, preventing separation of the rotary part 200 from the housing 110.

Figure 30:
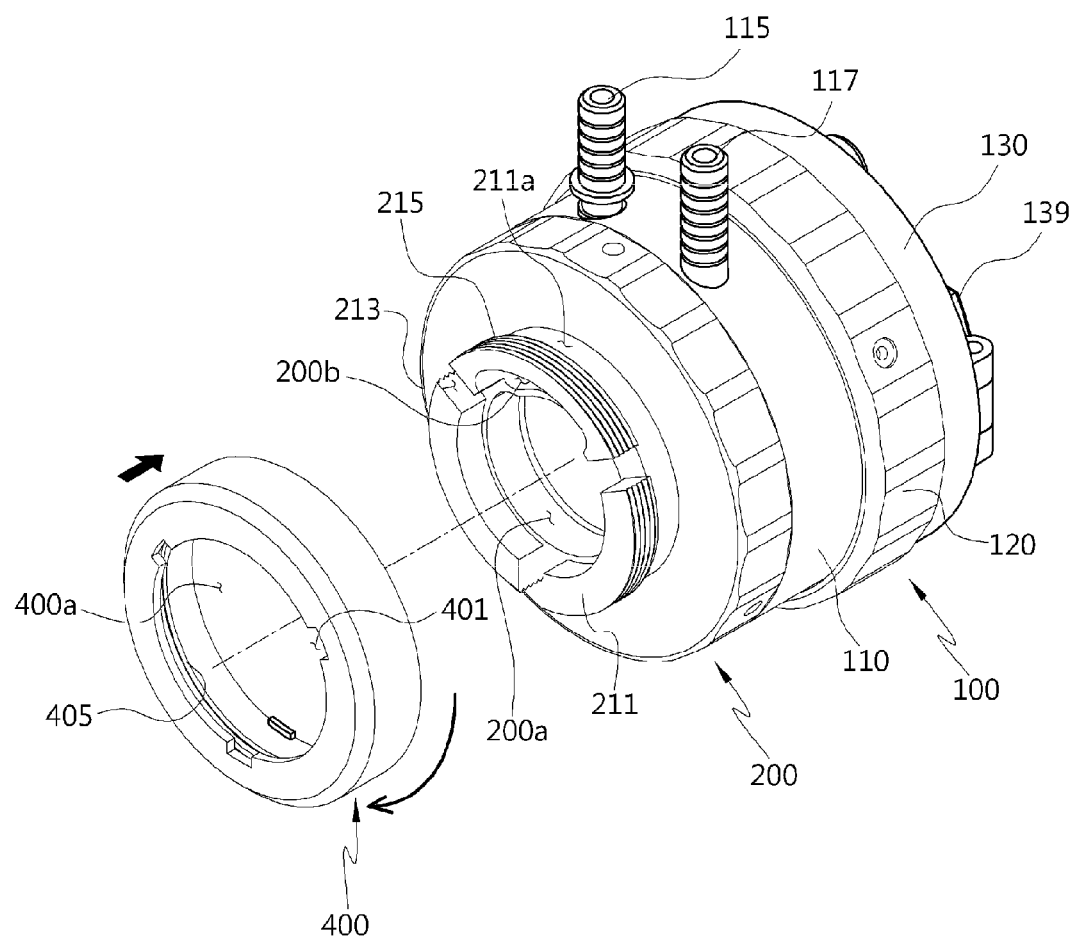

Next, as shown in FIG. 30, the barrel fixing part 400 is coupled to a front end of the rotary part 200. Here, after inserting the anti-separation protrusion 403 of the barrel fixing part 400 into the fixing hole 213 of the rotary part 200, the barrel fixing part 400 is rotated to threadedly fasten the rotary part 200 to the barrel fixing part 400.

Figure 31:
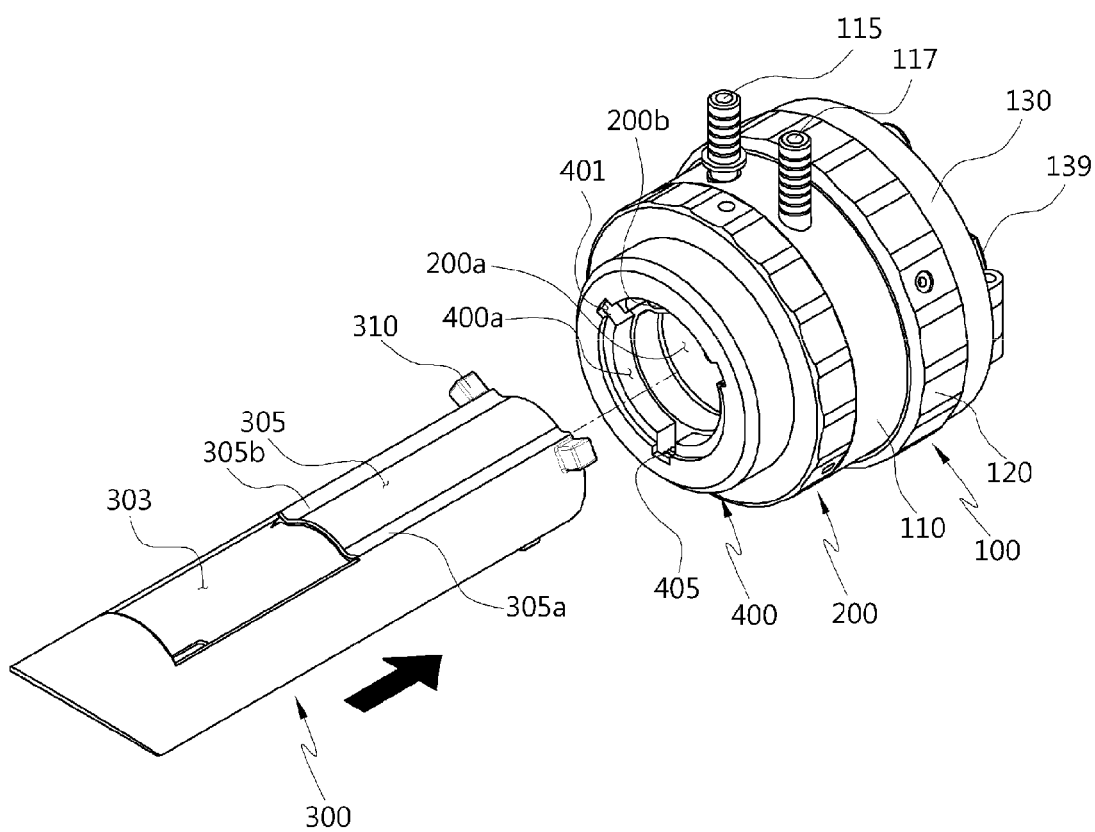

Next, as shown in FIG. 31, in a state in which the fixing hole 213 of the rotary part 200 is aligned with the through-hole 401 of the barrel fixing part 400, the fixing protrusion 310 of the barrel fixing part 300 is inserted into the through-hole 401 to insert the fixing protrusion 310 of the barrel fixing part 300 into the fixing hole 213 of the rotary part 200 when the barrel 300 is fully inserted into the barrel insertion hole 400a of the barrel fixing part 400.

Figure 32:
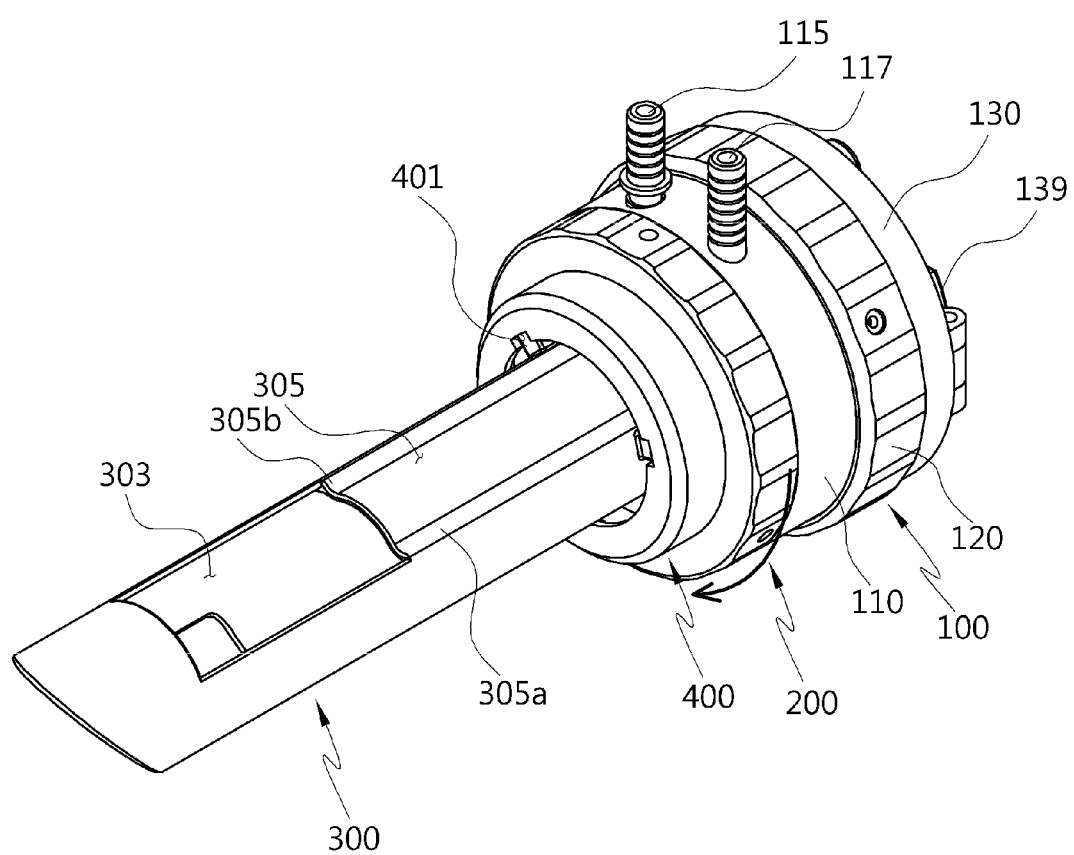

Then, as shown in FIG. 32, the barrel fixing part 400 is rotated to fix the barrel 300 to the rotary part 200.

Figure 33:
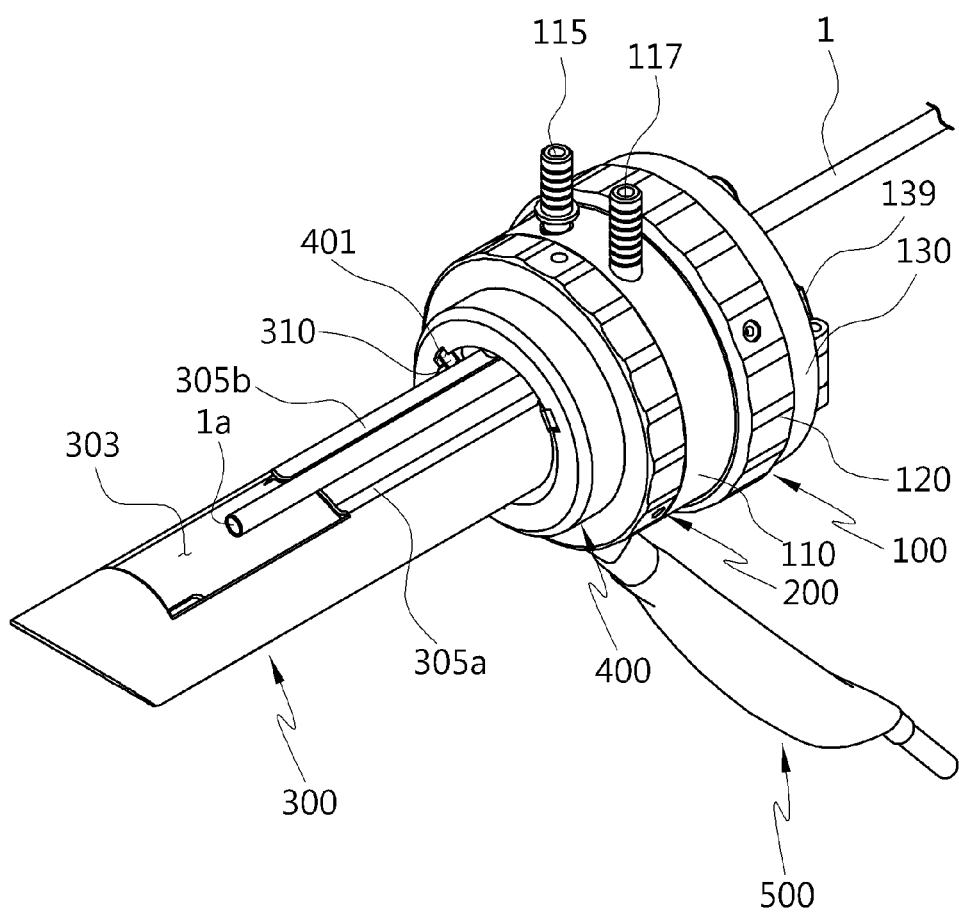

Next, as shown in FIG. 33, when the endoscope 1 is inserted through the endoscope insertion port 133 of the main body 100, the endoscope 1 passes through the main body 100 and the endoscope through-hole 200b of the rotary part 200 to be disposed outside the barrel 300. Here, since the tip 1a of the endoscope 1 is directed toward the inclined opening surface 301 through the endoscope open surface 303 of the barrel 300, a visual field for operation can be obtained. Therefore, the endoscope 1 is disposed outside the barrel 300 and the various surgical instruments are disposed inside the barrel 300 so that the outer diameter of the barrel 300 can be reduced to prevent interference between the endoscope 1 and the various surgical instruments. In addition, the outer diameter of the barrel 300 can be reduced to minimize probability of injury to the patient's anus.

Figure 34:
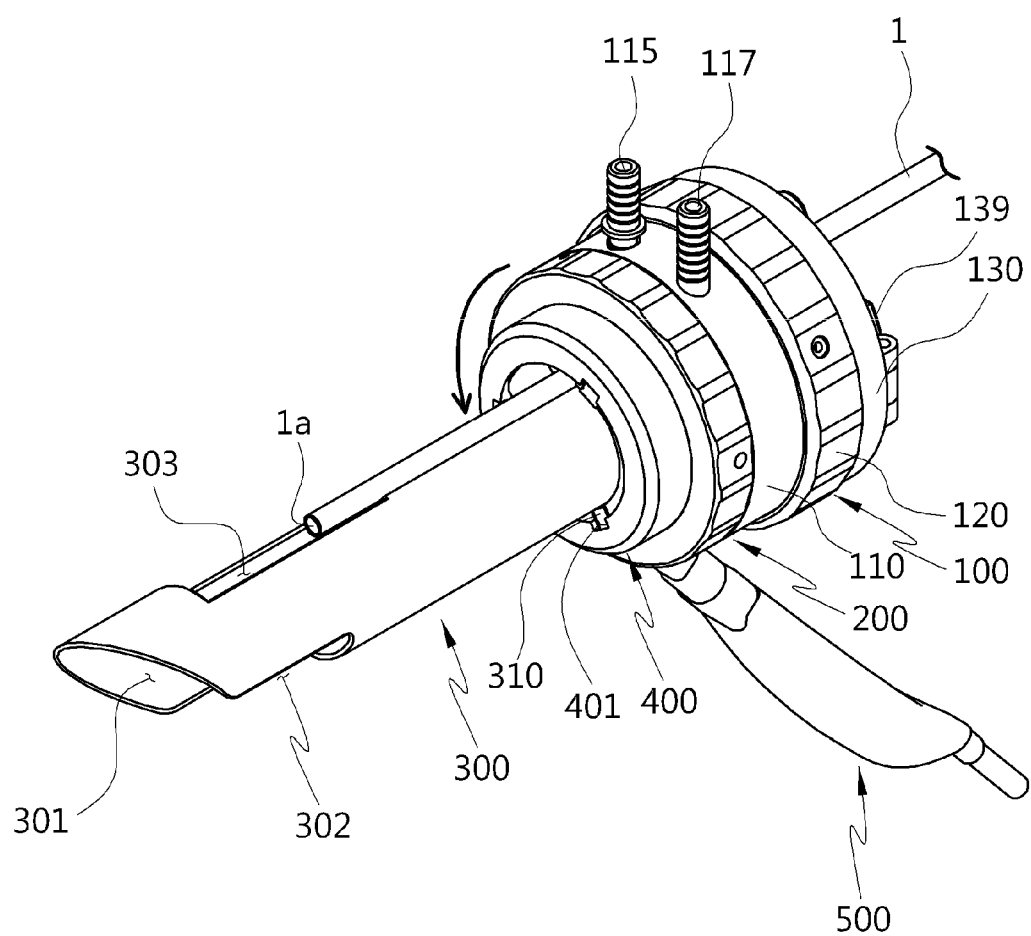
Figure 35:
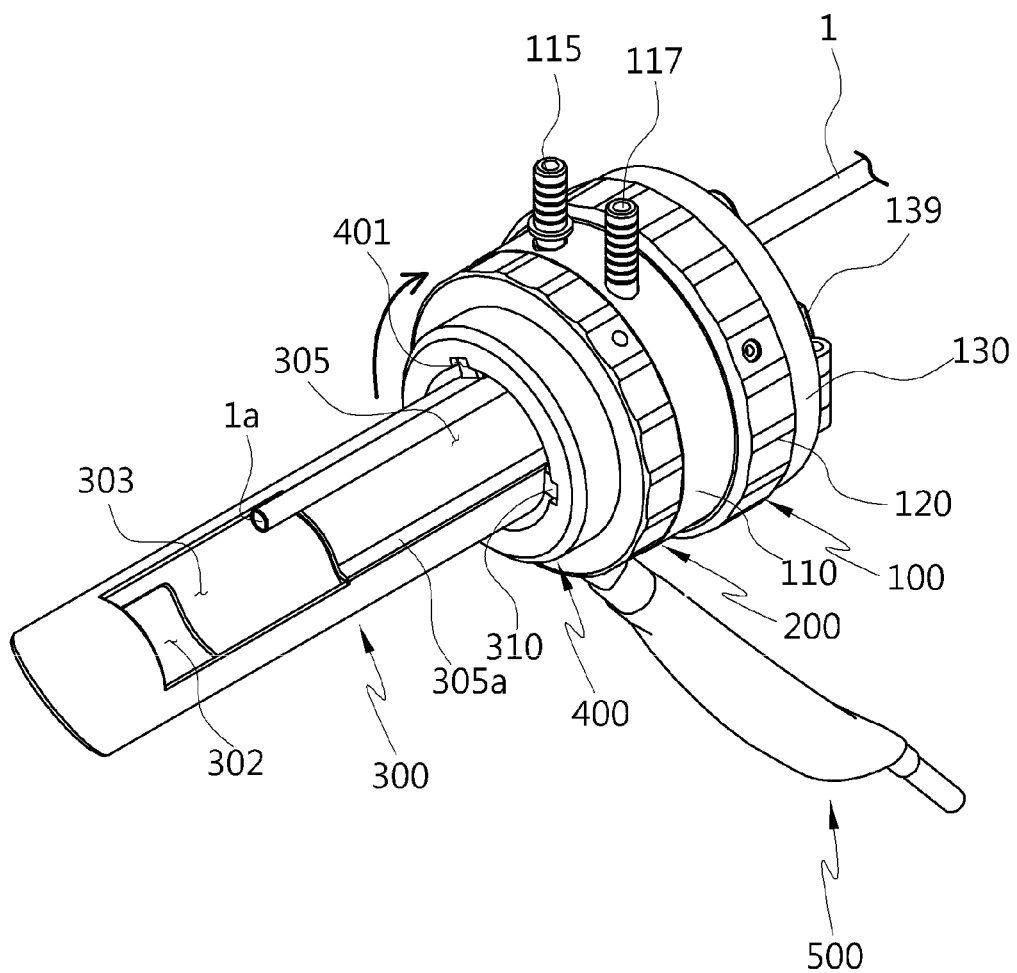

Next, when the barrel 300 is inserted into the patient's anus and an operation position is changed during the operation, as shown in FIGS. 34 and 35, in a state in which the surgical apparatus for TEM is fixed to the fixing frame (not shown), the barrel 300 can be manually rotated through lateral rotation of the rotary part 200 to a required amount. Here, since the endoscope 1 is fixedly disposed to the exterior of the barrel 300, there is no influence from lateral rotation of the barrel 300. Therefore, since there is no necessity to rotate the surgical apparatus 10 for TEM or move the patient after separation of the apparatus from the fixing frame, it is possible to increase convenience for a surgeon upon operation and minimize probability of medical accidents. In addition, rotation of the rotary part 200 causes rotation of the barrel 300 to obtain a visual field of a dead angle, which was hidden by the barrel 300, readily enlarging an operation range. Further, through variation in inclination angle of the tip of the barrel 300 and formation of the enlarged opening surface 302, the diameter of the barrel can be reduced according to the patient's body type to widen a moving area of the surgical instruments and the endoscope 1, the sizes of which are also reduced therewith.

Figure 36:
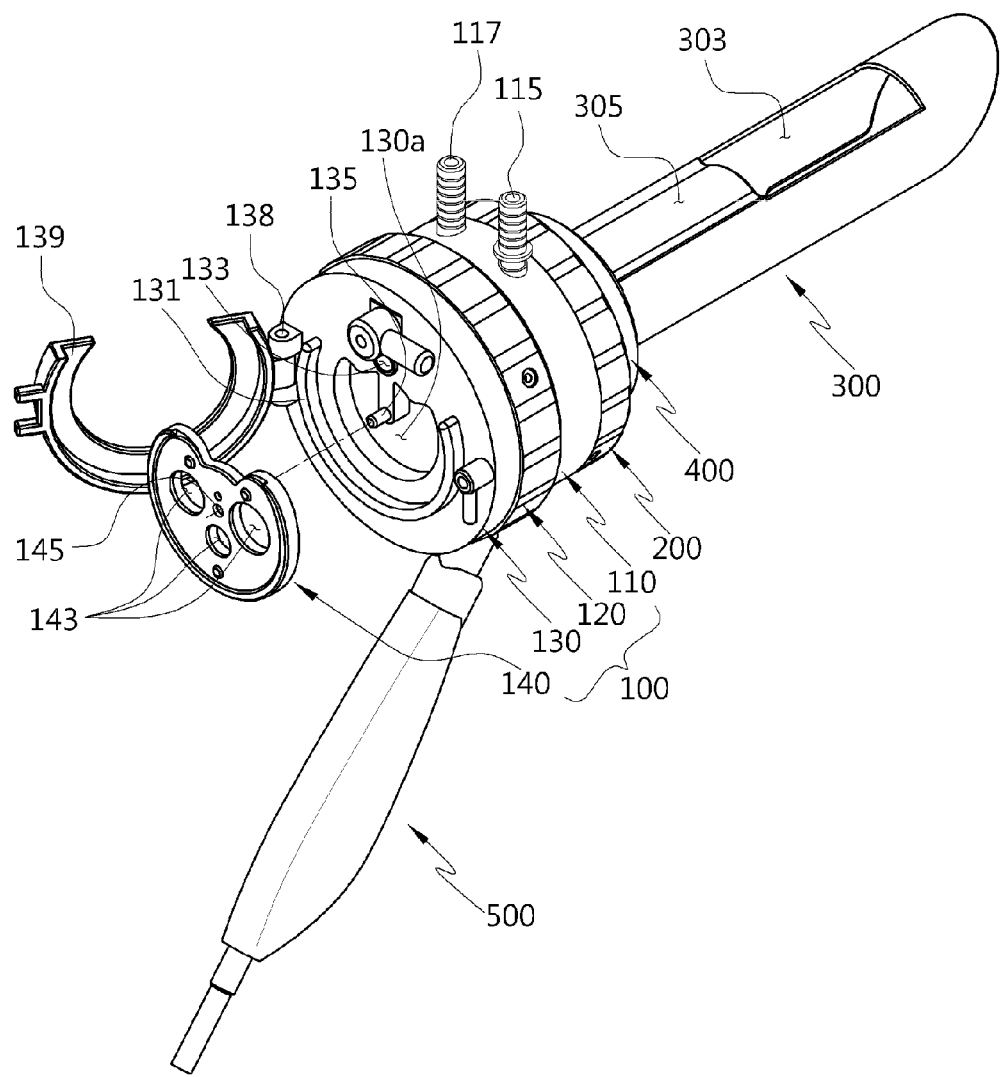

Next, as shown in FIG. 36, a tool insertion cover 139 hinged to the tool insertion part 130 having the endoscope insertion port 133 is opened, and the surgical instrument insertion part 140 having the surgical instrument insertion ports 143 is rotatably coupled to the rotary shaft protrusion 135 of the tool insertion part 130. Here, the surgical instrument insertion part is supported to be rotatably guided about the rotary shaft protrusion 135 by the rotation guide member 131 formed at the rear surface of the tool insertion part 130.

Figure 37:
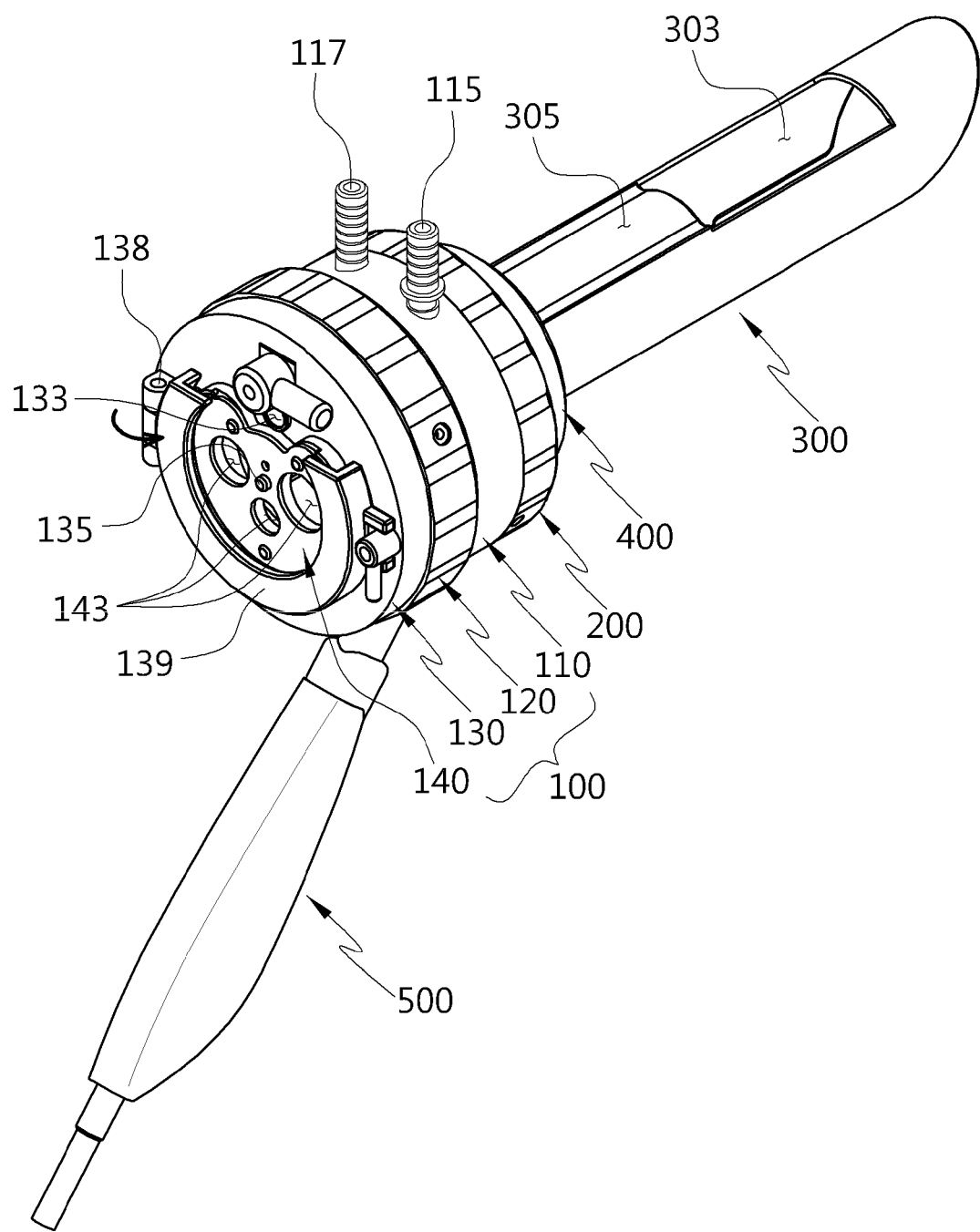

Next, as shown in FIG. 37, the tool insertion cover 139 is closed to prevent separation of the surgical instrument insertion part 140.

Figure 38:
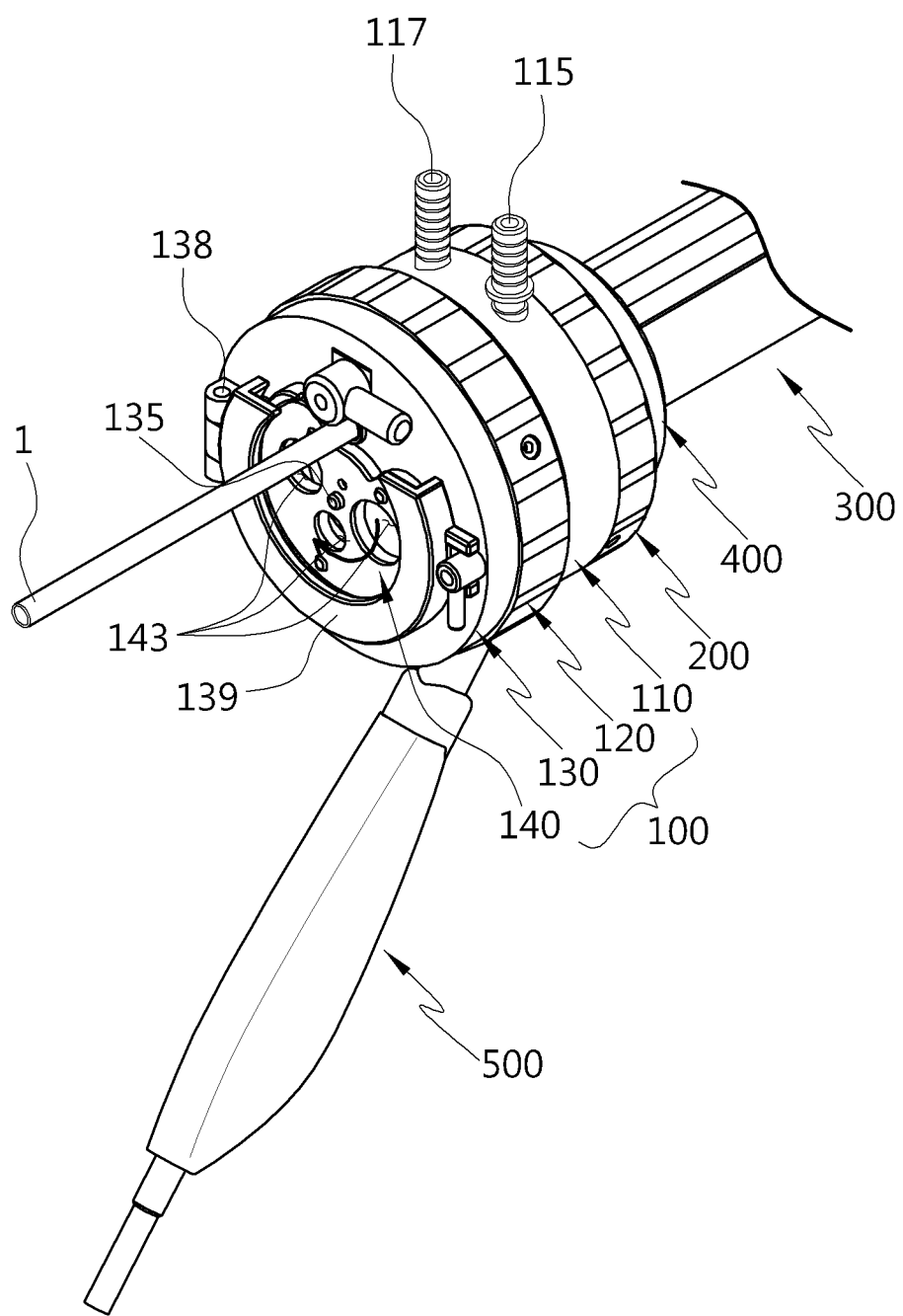
Figure 39:
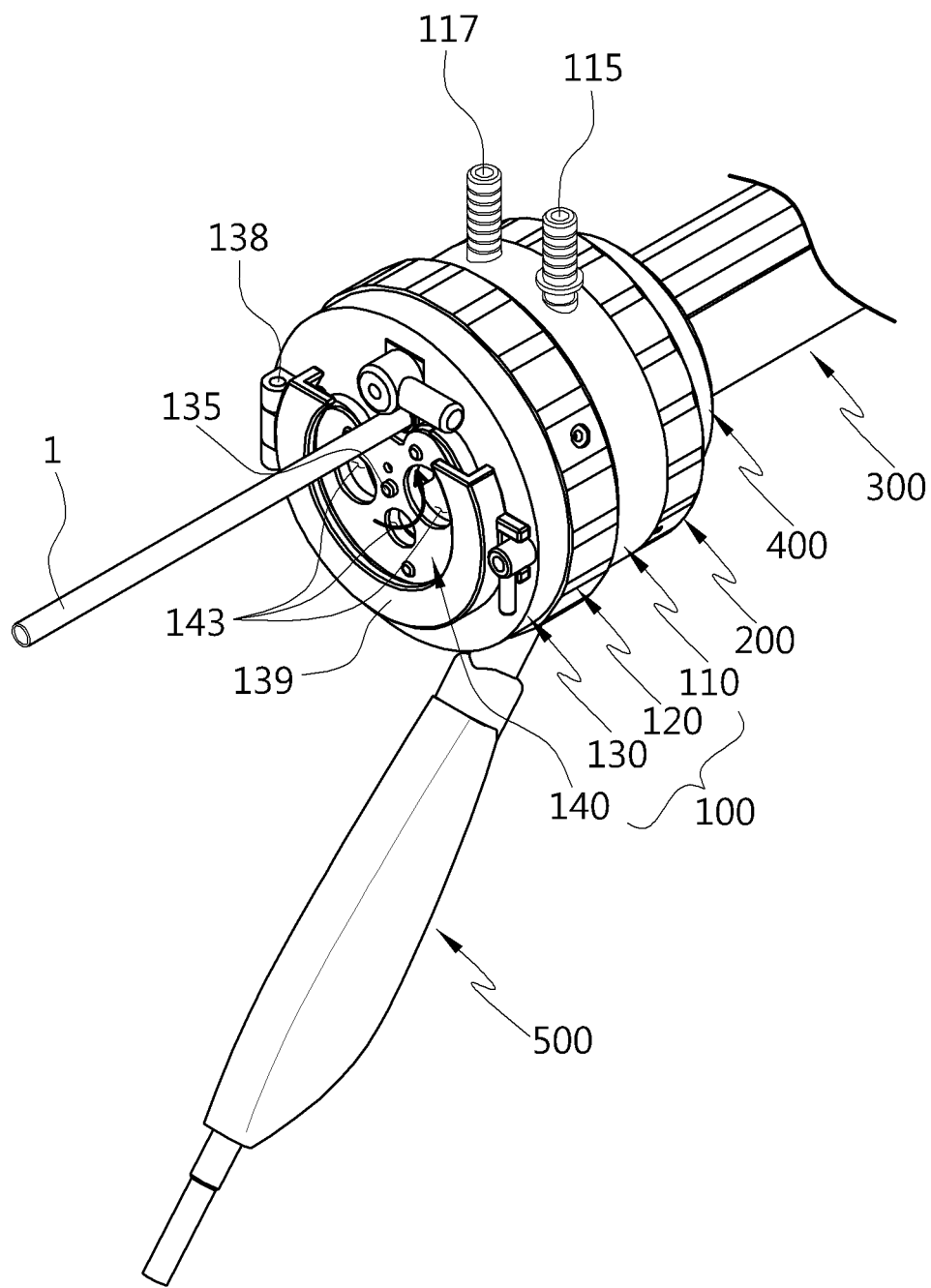

Next, as shown in FIGS. 38 and 39, the endoscope 1 is inserted through the endoscope insertion port 133 of the tool insertion part 130 and fixed thereto, and the surgical instruments are inserted through the surgical instrument insertion ports 143 of the surgical instrument insertion part 140. In addition, when the surgical instruments are laterally rotated, only the surgical instrument insertion port 143 is rotated separately from the endoscope insertion port 133 such that the surgical instruments can be freely moved without any interference with the endoscope 1. Here, an anti-interference groove 147 is formed at an upper edge of the surgical instrument insertion part 140 opposite to the endoscope 1 to correspond to a lateral rotation angle range of the surgical instrument insertion part 140 to prevent interference with the endoscope upon lateral rotation of the surgical instrument insertion part 140. In addition, since the surgical instrument insertion port 143 is separately rotated from the endoscope insertion port 133, a visual direction of the endoscope 1 can be uniformly maintained even when the barrel 300 and the various surgical instruments are rotated. As a result of uniformly maintaining the visual field of the endoscope 1, it is possible to prevent an operation image through the endoscope 1 from shaking or moving.

As can be seen from the foregoing, according to the surgical apparatus for TEM in accordance with the present invention, the barrel of the surgical apparatus for TEM further has a rotation function to provide operation convenience to a surgeon and minimize probability of medical accidents by manually rotating the barrel to a desired extent in a state in which the surgical apparatus for TEM is fixed to the fixing frame, when rotation of the surgical apparatus for TEM is needed to change an operation area.

In addition, since the barrel can be rotated to obtain a visual field at a dead angle, which was hidden by the barrel, it is possible to easily enlarge an operation range.

Further, since the endoscope is disposed outside the barrel, even when the barrel is rotated, the visual field of the endoscope can be uniformly maintained to prevent an operation image through the endoscope from shaking or moving.

Furthermore, since the endoscope is disposed outside the barrel, it is possible to reduce the outer diameter of the barrel inserted into a patient's anus, minimizing probability of injury to the anus.

In addition, the visual field of the endoscope and the moving range of the surgical instruments, which are decreased by reduction in diameter of the barrel, may be enlarged by variation in inclination angle of the tip of the barrel and formation of the enlarged opening surface.

Further, since the surgical instrument insertion port can be separately rotated from the endoscope insertion port, the surgical instruments can be more freely moved without any interference with the endoscope screen.

While the invention has been shown and described with reference to certain example embodiments thereof, it will be understood by those skilled in the art that various changes in form and details may be made therein without departing from the spirit and scope of the invention as defined by the appended claims.

What is claimed is:

1. A surgical apparatus for transanal endoscopic microsurgery (TEM), comprising:
   a main body having an endoscope insertion port through which an endoscope for TEM is inserted and a surgical instrument insertion port through which a surgical instrument is inserted, the surgical instrument insertion port being independently rotated from the endoscope insertion port;
   a rotary part rotatably coupled to a front end of the main body and through which the endoscope and the surgical instruments inserted into the main body pass; and
   a barrel coupled to a front end of the rotary part to be integrally rotated according to rotation of the rotary part, and inserted into the patient's anus to form a guide path for the endoscope and the surgical instrument,
   wherein the endoscope inserted into the main body and passing through the rotary part is disposed outside the barrel and the surgical instrument is disposed in the barrel.

2. The surgical apparatus for TEM according to claim 1, wherein the main body comprises:
   a housing having a front end to which the rotary part is rotatably coupled, and through which the endoscope and the surgical instrument pass;
   a tool insertion part coupled to a rear surface of the housing and in which the endoscope insertion port is formed; and
   a surgical instrument insertion part rotatably installed at the tool insertion part and in which the surgical instrument insertion port is formed.

3. The surgical apparatus for TEM according to claim 2, wherein the housing is configured to differentiate an endoscope through-hole through which the endoscope passes from a surgical instrument through-hole through which the surgical instrument passes.

4. The surgical apparatus for TEM according to claim 2, wherein a rotary shaft projection is formed at a center of a rear surface of the tool insertion part such that the surgical instrument insertion part is laterally rotatably coupled to the tool insertion part, and a rotary shaft groove is formed at a rotation center of the surgical instrument insertion part to receive the rotary shaft projection.

5. The surgical apparatus for TEM according to claim 4, wherein the tool insertion part has a surgical instrument through-hole opened around the rotary shaft projection to include a rotation angle range of the surgical instrument insertion port.

6. The surgical apparatus for TEM according to claim 2, wherein the tool insertion part comprises a rotation guide member configured to support the surgical instrument insertion part to be rotatably guided.

7. The surgical apparatus for TEM according to claim 6, wherein the tool insertion part comprises a tool insertion cover configured to prevent separation of the surgical instrument insertion part supported by the rotation guide member.

8. The surgical apparatus for TEM according to claim 2, wherein the surgical instrument insertion part has an anti-interference groove formed at a periphery of the surgical instrument insertion part opposite to the endoscope and corresponding to the rotation angle range of the surgical instrument insertion part to prevent interference with the endoscope upon rotation thereof.

9. The surgical apparatus for TEM according to claim 2, wherein the main body further comprises a locking part disposed between the housing and the tool insertion part and configured to lock the tool insertion part to the housing.

10. The surgical apparatus for TEM according to claim 1, wherein a rotation angle adjustment unit is installed between the main body and the rotary part to uniformly adjust a rotation angle of the rotary part in a stepped manner when the rotary part is rotated with respect to the main body.

11. The surgical apparatus for TEM according to claim 10, wherein the rotation angle adjustment unit comprises:
at least one click ball provided on a circumference of a front surface of the main body; and
a plurality of click grooves formed at a circumference of a rear surface of the rotary part at predetermined intervals,
wherein the click ball is inserted into the click grooves in a stepped manner to rotate the rotary part to a certain angle with respect to the main body when the rotary part is rotated.

12. The surgical apparatus for TEM according to claim 10, wherein the rotation angle adjustment unit comprises:
at least one first ring installed at an outer periphery of a front surface of the main body; and
a plurality of second rings installed along an inner periphery of a rear surface of the rotary part at predetermined intervals,
wherein the first ring is in contact with the second rings in a rotation direction thereof in a stepped manner to rotate the rotary part to a certain angle with respect to the main body when the rotary part is rotated.

13. The surgical apparatus for TEM according to claim 1, wherein an anti-separation unit is provided between the main body and the rotary part to prevent separation of the rotary part from the main body.

14. The surgical apparatus for TEM according to claim 13, wherein the anti-separation unit comprises:
an anti-separation groove formed along an outer periphery of a front end of the main body; and
an anti-separation screw inserted through a screw hole formed at a position of the rotary part corresponding to the anti-separation groove to be hooked by the anti-separation groove.

15. The surgical apparatus for TEM according to claim 1, wherein the barrel comprises an inclined opening surface having an opening formed at the barrel's tip and the inclined opening surface is inclined with respect to a longitudinal direction of the barrel.

16. The surgical apparatus for TEM according to claim 15, wherein the barrel comprises an enlarged opening surface configured to enlarge a lower area of the opening by extending a lower part of the inclined opening surface rearward.

17. The surgical apparatus for TEM according to claim 1, wherein the barrel comprises an endoscope opening surface having an opening corresponding to the tip of the endoscope disposed outside the barrel.

18. The surgical apparatus for TEM according to claim 1, further comprising a barrel fixing part coupled to the front end of the rotary part and configured to fix the barrel to the rotary part.

19. A surgical apparatus for transparent endoscopic microsurgery (TEM), comprising:
a main body into which an endoscope and surgical instruments for TEM are inserted;
a rotary part rotatably coupled to a front end of the main body and through which the endoscope and the surgical instruments inserted into the main body pass; and
a barrel coupled to a front end of the rotary part to be integrally rotated according to rotation of the rotary part, and inserted into the patient's anus to form a guide path for the endoscope and the surgical instruments,
wherein the endoscope inserted into the main body and passing through the rotary part is disposed outside the barrel and the surgical instruments are disposed in the barrel.

* * * * *